United States Patent

Hall et al.

[11] Patent Number: 4,582,854
[45] Date of Patent: Apr. 15, 1986

[54] 7-OXABICYCLOHEPTANE SUBSTITUTED OXA PROSTAGLANDIN ANALGOS USEFUL IN THE TREATMENT OF THROMBOLYTIC DISEASE

[75] Inventors: Steven E. Hall, Ewing Township, Mercer County; Martin F. Haslanger, Lambertville, both of N.J.

[73] Assignee: E. R. Squibb & Sons, Inc., Princeton, N.J.

[21] Appl. No.: 653,276

[22] Filed: Sep. 24, 1984

Related U.S. Application Data

[63] Continuation-in-part of Ser. No. 584,694, Feb. 29, 1984, abandoned, which is a continuation-in-part of Ser. No. 523,320, Aug. 15, 1983, abandoned.

[51] Int. Cl.[4] .................. A61K 31/34; A61K 31/557; C07D 307/00
[52] U.S. Cl. ..................................... 514/469; 549/463
[58] Field of Search ......................... 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted oxo prostaglandin analogs are provided having the structural formula

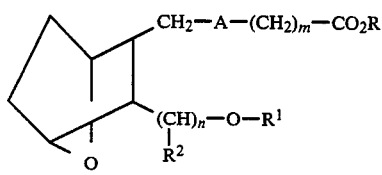

wherein R is hydrogen, lower alkyl, alkali metal or trihydroxymethylaminomethane, $R^1$ is lower alkyl, aryl, aralkyl, cycloalkyl or cycloalkylalkyl, $R^2$ is hydrogen or lower alkyl, A is $-CH=CH-$ or $-(CH_2)_2-$, n is 1 to 4, and m is 1 to 8, and including all stereoisomers thereof.

The compounds are cardiovascular agents useful, for example, in the treatment of thrombolytic disease.

35 Claims, No Drawings

7-OXABICYCLOHEPTANE SUBSTITUTED OXA PROSTAGLANDIN ANALGOS USEFUL IN THE TREATMENT OF THROMBOLYTIC DISEASE

REFERENCE TO OTHER APPLICATIONS

This application is a continuation-in-part of U.S. patent application Ser. No. 584,694, filed Feb. 29, 1984, now abandoned, which is a continuation-in-part of U.S. patent application Ser. No. 523,320, filed Aug. 15, 1983, now abandoned.

DESCRIPTION OF THE INVENTION

The present invention relates to 7-oxabicycloheptane oxa prostaglandin analogs which are cardiovascular agents useful, for example, in the treatment of thrombolytic disease. These compounds have the structural formula

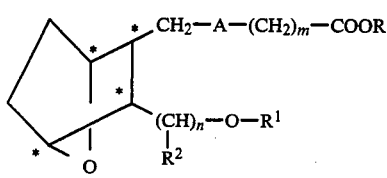

and including all stereoisomers thereof, wherein

A is CH=CH or $(CH_2)_2$, m is 1 to 8, n is 1 to 4, R is H, lower alkyl, alkali metal or tris(hydroxymethyl-)aminomethane, $R^1$ is lower alkyl, aryl, aralkyl, cycloalkyl or cycloalkylalkyl, and $R^2$ is H or lower alkyl, but where $R^2$ is lower alkyl, n is 1.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an alkylthio substituent, an alkylamino substituent (e.g., $R^3NH-$ or $(R^3)_2N-$ wherein $R^3$ is lower alkyl), a haloaryl substituent, a cycloalkyl substituent (that is, cycloalkylalkyl) or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "$(CH_2)_m$" includes a straight or branched chain radical having from 1 to 8 carbons and may contain one or more lower alkyl substituents. Examples of $(CH_2)_m$ groups and $(CH)_n$ groups (where appropriate) include

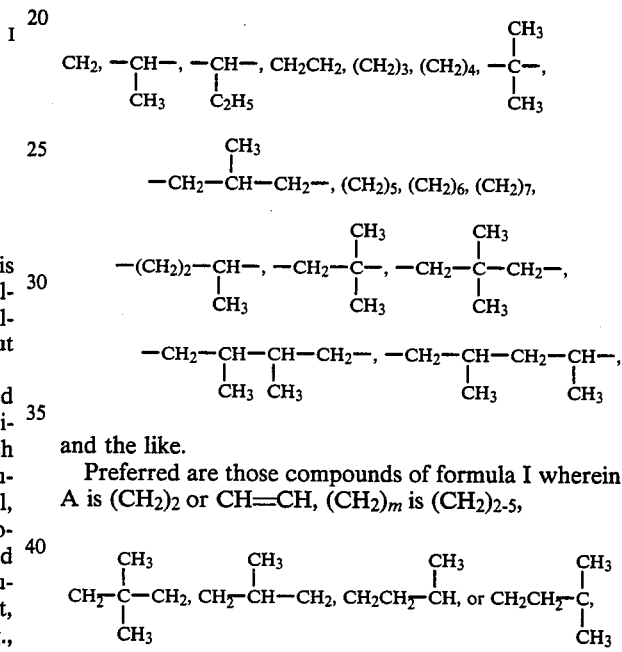

and the like.

Preferred are those compounds of formula I wherein A is $(CH_2)_2$ or CH=CH, $(CH_2)_m$ is $(CH_2)_{2-5}$, $$CH_3-\overset{CH_3}{\underset{CH_3}{C}}-CH_2,\ CH_2-\overset{CH_3}{CH}-CH_2,\ CH_2CH_2-\overset{CH_3}{CH},\ or\ CH_2CH_2-\overset{CH_3}{\underset{CH_3}{C}},$$

R is H, n is 1, 2 or 3, $R^1$ is pentyl, hexyl, cyclohexyl, cyclohexylmethyl, phenyl, benzyl, 2-phenylethyl or 3-phenylpropyl and $R^2$ is H, methyl or ethyl.

The various compounds of the invention may be prepared as outlined below.

A. where n = 1 and A is —CH=CH—

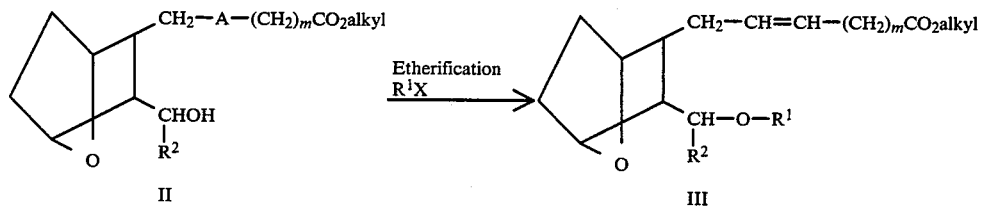

B. where n = 1 and A is —$(CH_2)_2$—

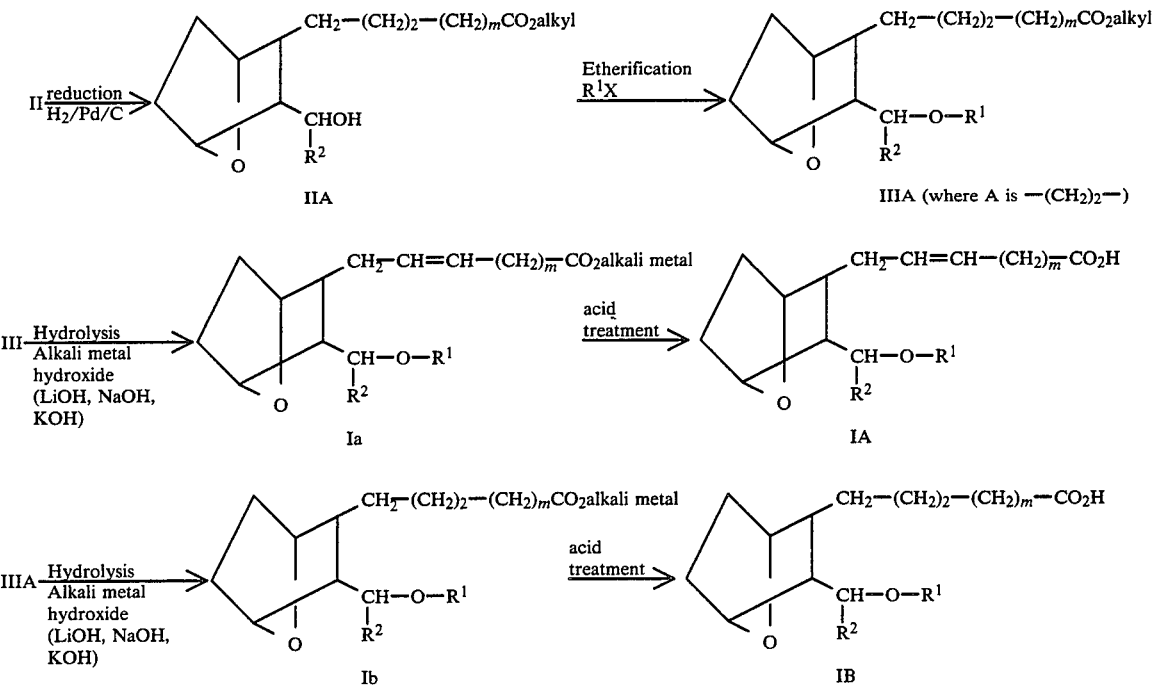
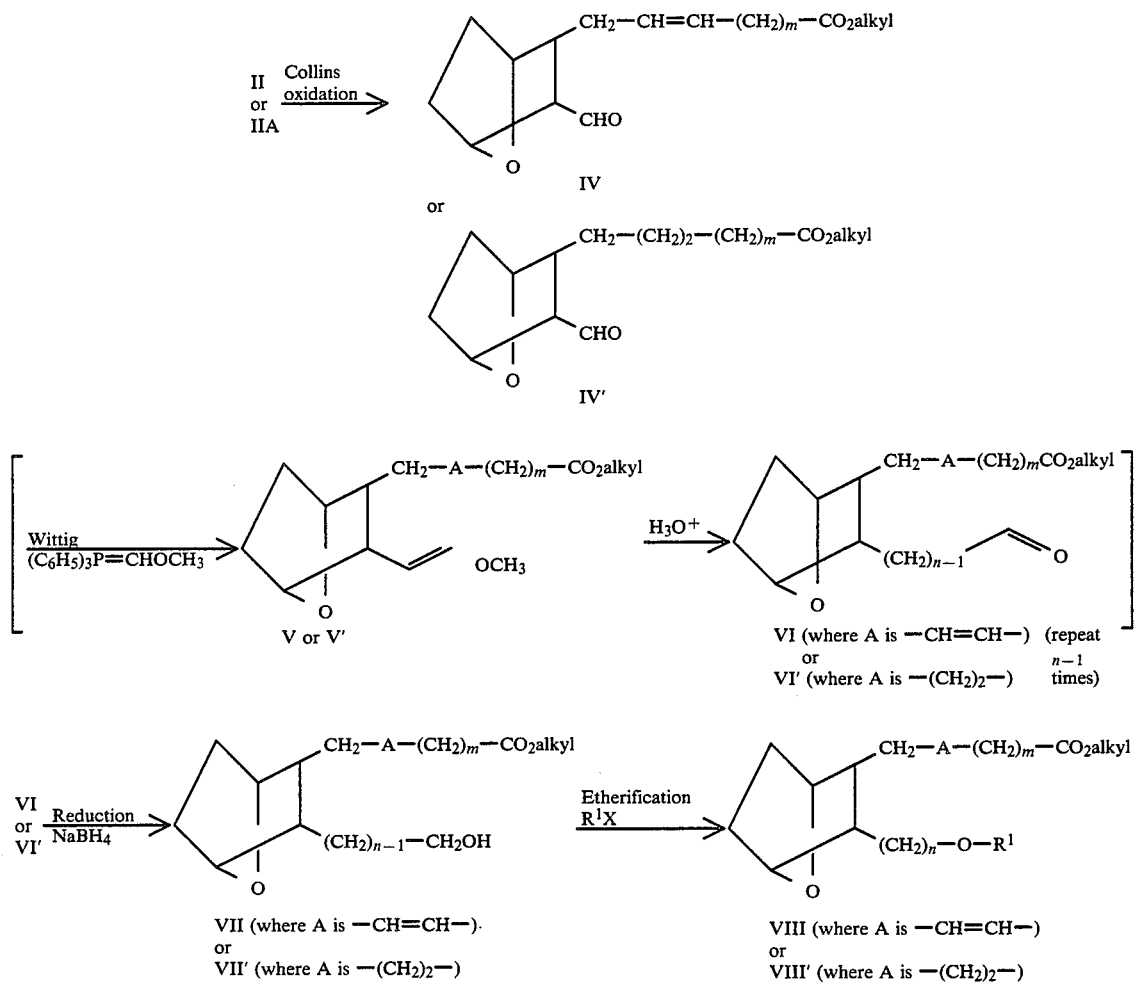
c. Where n is 2 to 4

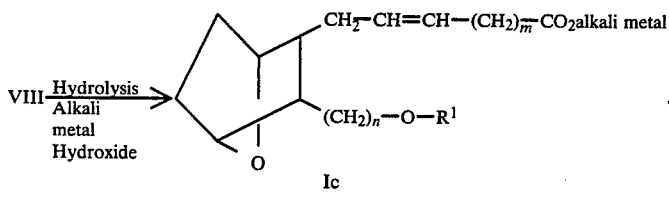

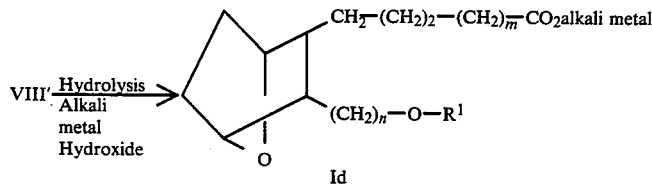

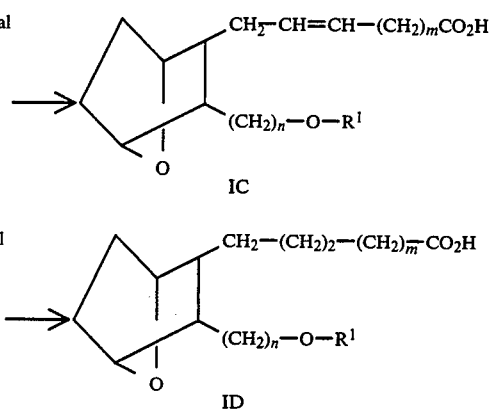

In the reaction sequence identified as "A", where in Formula I n is 1, the lower alkyl ester containing the hydroxymethyl group, that is, compound II (where A is —CH=CH—) or IIA (where A is —(CH$_2$)$_2$) (prepared as described in U.S. Pat. No. 4,143,054) is employed as the starting material. Thus, where A is —CH=CH—, compound II is subjected to an etherification reaction, for example, by reacting a compound of the structure

R$^1$X      A (wherein X is Cl, Br, I, OSO$_2$CH$_3$ or

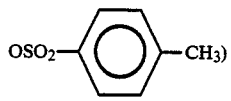

in the presence of a strong inorganic base such as KOH or NaOH, and an appropriate solvent to form ester III. To form the ester IIIA (where A is (CH$_2$)$_2$), (Reaction sequence "B"), compound II is reduced, for example with hydrogen over a palladium on carbon catalyst, to form hydroxymethyl compound IIA (where A is (CH$_2$)$_2$) and compound IIA is subjected to an etherification reaction as described above to form ester IIIA (where A is (CH$_2$)$_2$). In carrying out the above reaction, the hydroxymethyl compound II or IIA is employed in a molar ratio to the halide A, that is, II or IIA:A of within the range of from about 0.8:1 to about 1:5, employing a solvent such as xylene, tetrahydrofuran (THF), dimethylsulfoxide (DMSO) or dimethylformamide (DMF).

Where in R$^1$X, X is Br or Cl, a phase transfer etherification is employed in which case THF is used as the solvent and a phase transfer reagent such as Bu$_4$N-HSO$_4$, or (C$_6$H$_5$CH$_2$)(CH$_3$)$_3$NHSO$_4$ is employed.

The starting alcohol II wherein R$^2$ is lower alkyl may be prepared by reacting the aldehyde B

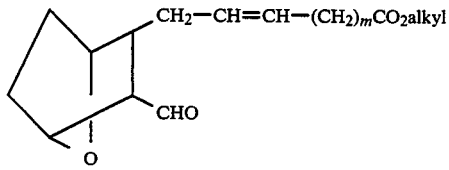

prepared as described in U.S. Pat. No. 4,143,054 with an alkyl Mg halide C of the structure R$^2$MgX (wherein X is Cl or Br)      C at reduced temperatures of less than about 0° C. in the presence of an inert organic solvent such as tetrahydrofuran.

In the reaction sequence identified as "C", where in Formula I n is 2 to 4, the starting lower alkyl ester containing the hydroxymethyl group, that is, compound II, (prepared as described in U.S. Pat. No. 4,143,054) is used to form the aldehyde IV (where A is —CH=CH—) or IV' (where A is —(CH$_2$)$_2$). Thus, to form aldehyde IV where A is —CH=CH—, compound II is subjected to a Collins oxidation, for example, by reacting II with chromium trioxide in pyridine. To form the aldehyde IV' (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IV' (where A is (CH$_2$)$_2$).

The aldehyde IV or IV' is used to prepare aldehyde VI or VI' (where n is 2-4) by carrying out a homologation sequence, such as a Wittig reaction with (C$_6$H$_5$)$_3$P=CHOMe followed by hydrolysis, (n−1) times. The aldehyde VI or VI' (where n is 2-4) is thus carried on to compounds of this invention where n is 2-4, that is

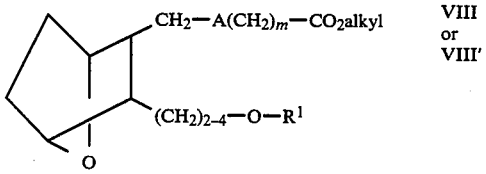

(VIII where A is =CH=CH—)
(VIII' where A is (CH$_2$)$_2$)

by reducing aldehyde VI or VI' employing a reducing agent such as sodium borohydride or sodium cyanoborohydride in a solvent such as methanol to form the alcohol ester VII or VII' which is subjected to an etherification reaction as described above to form VIII or VIII'.

Compounds of formula I wherein R$^1$ is aryl such as phenyl or substituted phenyl may be prepared by reacting the alcohol II or IIA or VII or VII' with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

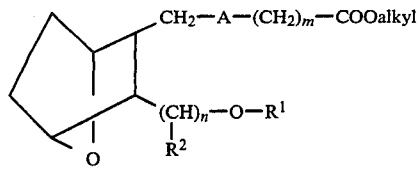
IX wherein $R^1$ is phenyl or substituted phenyl.

The starting alcohol II wherein $(CH_2)_m$ is

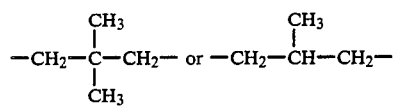

may be prepared as described in U.S. Pat. No. 4,143,054 or alternatively by subjecting the hemiacetal D

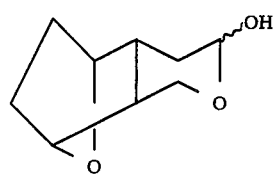
D to a Wittig reaction by treating hemiacetal D with the reaction product of carboxyalkyltriphenylphosphonium bromide E

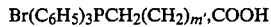
$Br(C_6H_5)_3PCH_2(CH_2)_{m'}COOH$    E wherein $(CH_2)_{m'}$ is

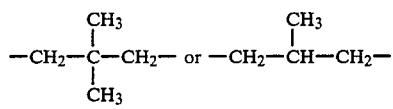

and potassium t-amylate and subsequently with diazomethane to form the alcohol IIB

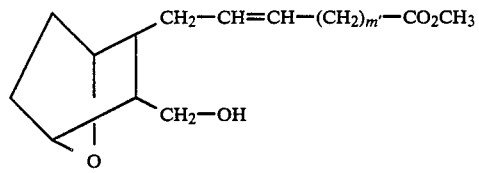
IIB

Alternatively, compounds of the invention wherein $(CH_2)_m$ is

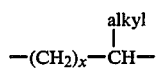
$-(CH_2)_x-CH-$ (wherein x is 1 to 7) may be prepared by simply reacting an ester X of the structure

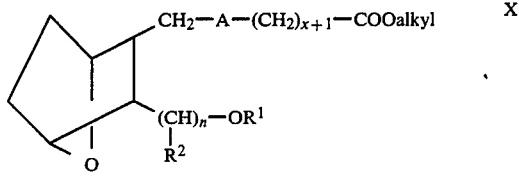
X prepared as described hereinbefore with lithium diisopropylamine and then treating the reaction with hexamethylphosphorous amide and an alkyl halide F at reduced temperatures alkyl—Hal     F wherein Hal is I, Br, or Cl
to form the ester XI

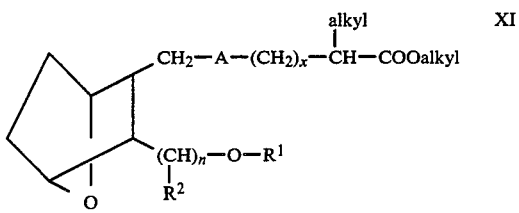
XI (wherein the above alkyls may be the same or different)

Compounds of the invention wherein $(CH_2)_m$ is

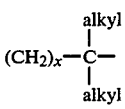

(wherein x is 1 to 7) may be prepared by reacting ester XI with lithium diisopropylamine and then treating the reaction with an alkyl halide F at reduced temperatures to form the ester XII

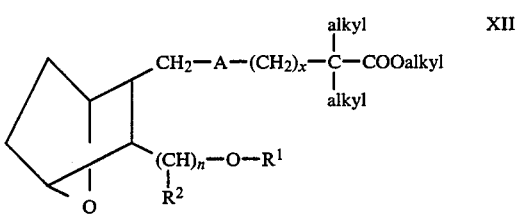
XII (wherein the R alkyl and the other alkyls may be the same or different)

The ester III, IIIA, VIII, VIII', IX, X, XI or XII can be converted to the free acid, that is, to

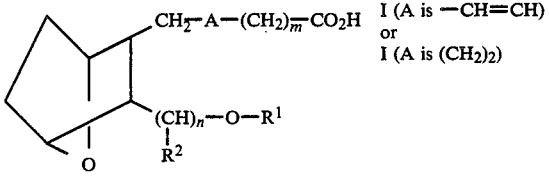
I (A is $-CH=CH$)
or
I (A is $(CH_2)_2$)

by treating the esters with an alkali metal hydroxide, such as lithium, sodium or potassium hydroxide to form the alkali metal salt Ia or Ib or Ic or Id, followed by neutralizing with an acid, such as dilute hydrochloric acid or oxalic acid to form the corresponding acid.

The tris(hydroxymethyl)aminomethane salt of any of the acids of formula I of the present invention is formed by reacting a solution of such acid in an inert solvent such as methanol with tris(hydroxymethyl)aminomethane and thereafter removing the solvent by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

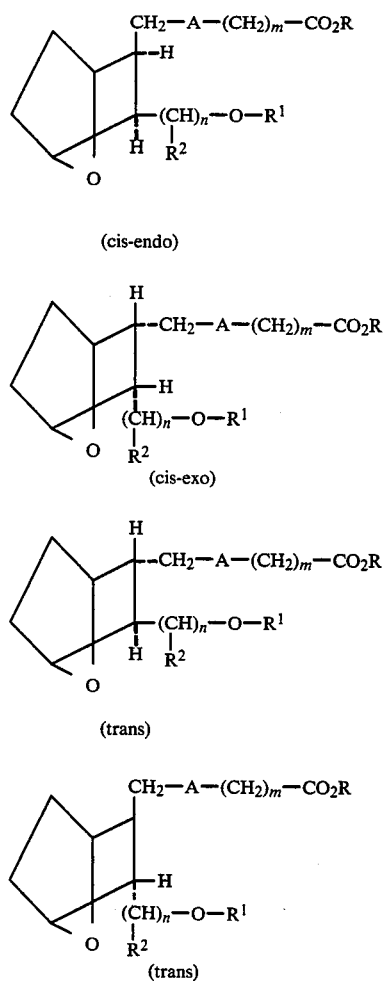

The nucleus in each of the compounds of the invention is depicted as

for matter of convenience; it will also be appreciated that the nucleus in the compounds of the invention may be depicted as

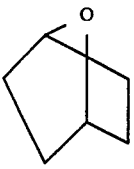

The compounds of this invention are cardiovascular agents useful as platelet aggregation inhibitors, such as in inhibiting arachidonic acid induced platelet aggregation, e.g., for treatment of thrombolytic disease, such as coronary or cerebral thromboses or in inhibiting bronchoconstriction, such as associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention.

EXAMPLE 1

[1β,2α(5Z),3α,4β]-7-[3-[(Hexyloxy)methyl]-7-oxabicyclo[2.2.1]hept-2-yl]-5-heptenoic acid, hexyl ester

A.

[1β,2α(5Z),3α,4β]-7-[3-(Hydroxymethyl)-7-oxabicyclo[2.2.1]hept-2-yl]-5-heptenoic acid, methyl ester (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml); the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane: yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gives an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing. This was recrystallized twice from ethyl acetate-cyclohexane to yield 320 mg of [1β,2α(5Z),3α,4β]-7-[3-(hydroxymethyl)-7-oxabicyclo[2.2.1]hept-2-yl]-5-heptenoic acid.

(d) Following the procedure as set out in Example 7 of U.S. Pat. No. 4,143,054, the acid from part (c) is converted to the corresponding methyl ester.

B.

[1β,2α(5Z),3α,4β]-7-[3-[(Hexyloxy)methyl]-7-oxabicyclo[2.2.1]hept-2-yl]-5-heptenoic acid, hexyl ester A suspension of 0.56 g of powdered KOH in 15 ml of dry xylene was heated to reflux and 7 ml of xylene was distilled off. To this mixture was added a solution of 300 mg (1.12 mmol) of alcohol ester from part A in 10 ml of dry xylene. The resulting mixture was heated to reflux and 9 ml of xylene was distilled off. To this mixture was added 1.0 g (5.6 mmol) of n-hexylmethanesulfonate and the resulting mixture was heated at reflux for 1½ hours. The reaction mixture was cooled to ambient temperature and diluted with $CH_2Cl_2$ (60 ml). The resulting solution was poured into 50 ml saturated $NaHCO_3$. The layers were separated and the aqueous phase was extracted (2×60 ml) with $CH_2Cl_2$. The combined $CH_2Cl_2$ extracts were dried over $MgSO_4$, then concentrated in vacuo to yield 0.9 g of crude product. The crude product was chromatographed on 33.4 g of silica gel 60 with hexane:ether (5:1) to yield 390 mg (83%) of the title hexyl ester.

EXAMPLE 2

[1β,2α(5Z),3α,4β]-7-[3-[(Hexyloxy)methyl]-7-oxabicyclo[2.2.1]hept-2-yl]-5-heptenoic acid To a stirred solution of 115 mg (0.27 mmol) of the Example 1 hexyl ester in 12.0 ml of distilled THF and 1.60 ml of $H_2O$ under argon was added 2.40 ml of 1N aqueous lithium hydroxide solution. This mixture was purged with argon for 40 minutes and stirred at room temperature for 24 hours. At this time, TLC analysis showed that the reaction was not complete so an additional 1 ml of methanol and 1 ml of 1N aqueous lithium hydroxide was added. The reaction mixture was kept stirring for another 4 hours and then was acidified to pH 4 by the addition of 1N aqueous HCl solution. The resulting solution was poured into 25 ml of saturated NaCl solution and was saturated wth solid NaCl. The aqueous layer was extracted with EtOAc (4×40 ml). The combined EtOAc extracts were dried over anhydrous $MgSO_4$, filtered and concentrated in vacuo to give 124 mg of crude oil. This was chromatographed on 20.6 g of silica gel 60 using hexane:ether (2:3) as eluant to give 102 mg of desired product contaminated with a small amount of hexyl alcohol. The mixture was put in high vacuum overnight at room temperature to give 77 mg (84%) of pure title acid. TLC: silica gel, 8% $CH_3OH/CH_2Cl_2$, $R_f=0.74$, iodine.

Anal. Calc'd for $C_{20}H_{34}O_4$: C, 70.97; H, 10.12; Found: C, 70.60; H, 9.89.

EXAMPLE 3

[1β,2α(5Z),3α,4β]-7-[3-[(Hexyloxy)methyl]-7-oxabicyclo[2.2.1]hept-2-yl]-5-heptenoic acid, hexyl ester 503 mg (1.88 mmol) of [1β,2α(5Z),3α,4β]-7-[3-(hydroxymethyl)-7-oxabicyclo[2.2.1]hept-2-yl]-5-heptenoic acid, methyl ester (prepared as described in Example 1) was dissolved in 2.17 ml tetrahydrofuran. Thereafter 2.17 ml (15.46 mmol) of n-hexyl bromide, 173.4 mg (0.51 mmol) tetrabutylammoniumbisulfate ($Bu_4NHSO_4$), and 2.17 ml of a 50% NaOH solution were added and the mixture vigorously stirred at room temperature. A slightly yellowish-brown solution formed which upon stirring overnight formed a white precipitate.

The reaction mixture was poured into 25 ml of saturated NaHCO$_3$. The mixture was extracted with CH$_2$Cl$_2$ (4×25 ml). The combined CH$_2$Cl$_2$ extracts were dried (MgSO$_4$), filtered and concentrated in vacuo to give [1β,2α(5Z),3α,4β]-7-[3-[(hexyloxy)methyl]-7-oxabicyclo[2.2.1]hept-2-yl]-5-heptenoic acid, hexyl ester (1272 mg). This was chromatographed on 40 g silica gel using hexane:ether (4:1) as eluant to give final product.

EXAMPLE 4

(1β,2α,3α,4β)-7-[3-[(Hexyloxy)methyl]-7-oxabicyclo[2.2.1]hept-2-yl]heptanoic acid, hexyl ester

A.

(1β,2α,3α,4β)-7-[3-[(Hydroxy)methyl]-7-oxabicyclo[2.2.1]hept-2-yl]heptanoic acid, methyl ester To 800 mg (3.0 mmole) of the [1β,2α(5Z),3α,4β]-7-[3-(hydroxymethyl)-7-oxabicyclo[2.2.1]heptenoic acid, methyl ester as prepared in Example 1, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1β,2α,3α,4β)-7-[3-[(Hexyloxy)methyl]-7-oxabicyclo[2.2.1]hept-2-yl]-5-heptanoic acid, hexyl ester Following the procedure of Example 1 except substituting the Part A alcohol-ester for the Example 1A alcohol ester, the title product is obtained.

EXAMPLE 5

(1β,2α,3α,4β)-7-[3-[(Hexyloxy)methyl]-7-oxabicyclo[2.2.1]hept-2-yl]heptanoic acid Following the procedure of Example 2 except substituting the Example 4 hexyl ester for the Example 1 hexyl ester, the title acid is obtained.

EXAMPLE 6

[1β,2α(5Z),3β,4β]-7-[3-[(Hexyloxy)methyl]-7-oxabicyclo[2.2.1]hept-2-yl]-5-heptenoic acid Following the procedure of Examples 3 and 2 except substituting [1β,2α(5Z),3β,4β]-7-[3-(hydroxymethyl)-7-oxabicyclo[2.2.1]hept-2-yl]-5-heptenoic acid, methyl ester (prepared as described in U.S. Pat. No. 4,143,054) for [1β,2α(5Z),3α,4β]-7-[3-(hydroxymethyl)-7-oxabicyclo[2.2.1]-hept-2-yl]-5-heptenoic acid, methyl ester, the title compound is obtained.

EXAMPLE 7

[1β,2α(5Z),3α,4β]-7-[3-(Methyloxy)methyl]-7-oxabicyclo[2.2.1]hept-2-yl]-5-heptenoic acid Following the procedure of Examples 1 and 2 except substituting methyl methanesulfonate for n-hexyl methanesulfonate, the title compound is obtained.

EXAMPLE 8

[1β,2α(5Z),3β,4β]-7-[3-[(Propyloxy)methyl]-7-oxabicyclo[2.2.1]hept-2-yl]-5-heptenoic acid Following the procedure of Example 6, except substituting n-propylbromide for n-hexylbromide, the title compound is obtained.

EXAMPLE 9

(1β,2α,3α,4β)-7-[3-[(Butyloxy)methyl]-7-oxabicyclo[2.2.1]hept-2-yl]heptanoic acid Following the procedure of Examples 4 and 5 except substituting n-butyl methanesulfonate for n-hexyl methanesulfonate, the title compound is obtained.

EXAMPLE 10

[1β,2α(5Z),3α,4β]-7-[3-[(Octyloxy)methyl]-7-oxabicyclo[2.2.1]hept-2-yl]-5-heptenoic acid Following the procedure of Examples 1 and 2 except substituting n-octyl methanesulfonate for n-hexyl methanesulfonate, the title compound is obtained.

EXAMPLE 11

[1β,2α(5Z),3α,4β]-7-[3-[(Phenyloxy)methyl]-7-oxabicyclo[2.2.1]hept-2-yl]-5-heptenoic acid (a) Phenol (1 mmol) is added to a solution of triphenylphosphine (1 mmol), diethylazodicarboxylate (1 mmol) and title A alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(5Z),3α,4β]-7-[3-[(phenyloxy)methyl]-7-oxabicyclo[2.2.1]hept-2-yl]-5-heptenoic acid, methyl ester.

(b) Following the procedure as set out in Example 2, the ester from part (a) is converted to the title compound.

EXAMPLE 12

[1β,2α(5Z),3β,4β]-7-[3-[(Phenyloxy)methyl]-7-oxabicyclo[2.2.1]hept-2-yl]-5-heptenoic acid (a) Phenol (1 mmol) is added to a solution of triphenylphosphine (1 mmol), diisopropylazodicarboxylate (1 mmol) and [1β,2α(Z),3β,4β]-7-[3-(hydroxymethyl)-7-oxabicyclo[2.2.1]hept-2-yl]-5-heptenoic acid (prepared as described in U.S. Pat. No. 4,143,054) (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(5Z),3β,4β]-7-[3-[(phenyloxy)methyl]-7-oxabicyclo[2.2.1]hept-2-yl]-5-heptenoic acid, methyl ester.

(b) Following the procedure as set out in Example 2, the ester from part (a) is converted to the title compound.

EXAMPLE 13

[1β,2α(5Z),3α,4β]-7-[3-[(Ethyloxy)methyl]-7-oxabicyclo[2.2.1]hept-2-yl]-5-heptenoic acid Following the procedure of Examples 3 and 2 except substituting ethylbromide for n-hexylbromide, the title compound is obtained.

EXAMPLE 14

(1β,2α,3α,4β]-7-[3-[(Phenyloxy)methyl]-7-oxabicyclo[2.2.1]hept-2-yl]heptanoic acid Following the procedure of Example 11 except substituting (1β,2α,3α,4β)-7-[3-[(hydroxy)methyl]-7-oxabicyclo[2.2.1]hept-2-yl]heptanoic acid, methyl ester for the alcohol of part (a) of Example 11, the title compound is obtained.

EXAMPLE 15

[1β,2α(5Z),3β,4β]-7-[3-[(Benzyloxy)methyl]-7-oxabicyclo[2.2.1]hept-2-yl]-5-heptenoic acid Following the procedure of Example 6 except substituting benzylbromide for n-hexylbromide, the title compound is obtained.

EXAMPLE 16

(1β,2α,3α,4β)-7-[3-[(Benzyloxy)methyl]-7-oxabicyclo[2.2.1]hept-2-yl]heptanoic acid Following the procedure of Examples 4 and 5 except substituting benzyl methanesulfonate for n-hexyl methanesulfonate, the title compound is obtained.

EXAMPLE 17

[1β,2α(5Z),3α,4β]-7-[3-[(Cyclohexyloxy)methyl]-7-oxabicyclo[2.2.1]hept-2-yl]-5-heptenoic acid Following the procedure of Examples 1 and 2 except substituting cyclohexyl methanesulfonate for n-hexyl methanesulfonate, the title compound is obtained.

EXAMPLE 18

[1β,2α(5Z),3β,4β]-7-[3-[(Cyclopentyloxy)methyl]-7-oxabicyclo[2.2.1]hept-2-yl]-5-heptenoic acid Following the procedure of Examples 1 and 2 except substituting cyclopentyl methanesulfonate for n-hexyl methanesulfonate, and substituting [1β,2α(Z),3β,4β]-7-[3-(hydroxymethyl)-7-oxabicyclo[2.2.1]hept-2-yl]-5-heptenoic acid, methyl ester (prepared as described in U.S. Pat. No. 4,143,054) for [1β,2α(5Z),3α,4β]-7-[3-(hydroxymethyl)-7-oxabicyclo[2.2.1]hept-2-yl]-5-heptanoic acid, methyl ester, the title compound is obtained.

EXAMPLE 19

(1β,2α,3α,4β)-7-[3-[(Cyclohexyloxy)methyl]-7-oxabicyclo[2.2.1]hept-2-yl]heptanoic acid Following the procedure of Examples 4 and 5 except substituting cyclohexyl methanesulfonate for n-hexyl methanesulfonate, the title compound is obtained.

EXAMPLE 20

[1β,2α(5Z),3α,4β]-7-[3-[2-(Hexyloxy)ethyl]-7-oxabicyclo[2.2.1]hept-2-yl]-5-heptenoic acid

A.

[1β,2α(5Z),3α,4β]-7-[3-(2-Oxo)ethyl]-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride $((C_6H_5)_3P^+—CH_2OCH_3Cl^-)$ and 235 ml distilled toluene (stored over molecular sieves). The resulting suspension was stirred in an ice-bath under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH4Cl, and extracted with ether (4×200 ml). The combined ether phases were washed with NaCl saturated solution, and dried (MgSO4) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl]-7-oxabicyclo[2.2.1]-hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with NaBH4 (0.19 g, 5 mmol) in an argon atmosphere at 0° C. After stirring at 0° for 1 hour, the reaction was quenched by addition of 2N HCl (to pH 2). The methanol was removed in vacuo and the reaction mixture was taken up in ether. The ether solution was washed with saturated KHCO3, saturated NaCl and dried (MgSO4). The ether was evaporated to yield the title B compound.

C.

[1β,2α(5Z),3α,4β]-7-[3-[2-(Hexyloxy)ethyl]-7-oxabicyclo[2.2.1]hept-2-yl]-5-heptenoic acid Following the procedure of Examples 1 and 2 except substituting the above part B alcohol for the alcohol used in Example 1, the title compound is obtained.

EXAMPLE 21

[1β,2α(5Z),3β,4β]-7-[3-[2-(Hexyloxy)ethyl]-7-oxabicyclo[2.2.1]hept-2-yl]-5-heptenoic acid Following the procedure of Example 20, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]-hept-2-yl]-5-heptenoic acid, methyl ester, the title compound is obtained.

EXAMPLE 22

(1β,2α,3α,4β)-7-[3-[2-(Hexyloxy)ethyl]-7-oxabicyclo[2.2.1]hept-2-yl]-5-heptanoic acid Following the procedure of Example 21 except substituting (1β,2α,3α,4β)-7-[3-formyl-7-oxabicyclo[2.2.1]hept-2-yl]heptanoic acid, methyl ester for [1β,2α(5Z),3β,4β]-7-[3-formyl-7-oxabicyclo[2.2.1]hept-2-yl]-5-heptenoic acid, methyl ester, the title compound is obtained.

EXAMPLE 23

[1β,2α(5Z),3β,4β]-7-[3-[2-(Phenyloxy)ethyl]-7-oxabicyclo[2.2.1]hept-2-yl]-5-heptenoic acid Following the procedure of Example 11 except substituting [1β,2α(5Z),3α,4β]-7-[3-[2-(hydroxy)ethyl]-7-oxabicyclo[2.2.1]hept-2-yl]-5-heptenoic acid, methyl ester for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 24

[1β,2α(5Z),3β,4β]-7-[3-[2-(Phenyloxy)ethyl]-7-oxabicyclo[2.2.1]hept-2-yl]-5-heptenoic acid Following the procedure of Example 12 except substituting [1β,2α(5Z),3β,4β]-7-[3-[2-(hydroxy)ethyl]-7-oxabicyclo[2.2.1]hept-2-yl]-5-heptenoic acid, methyl ester for [1β,2α(5Z),3β,4β]-7-[3-(hydroxymethyl)-7-oxabicyclo[2.2.1]hept-2-yl]-5-heptenoic acid, methyl ester, the title compound is obtained.

EXAMPLE 25

(1β,2α,3α,4β)-7-[3-[2-(Phenyloxy)ethyl]-7-oxabicyclo[2.2.1]hept-2-yl]heptanoic acid Following the procedure of Example 11 except substituting (1β,2α,3α,4β)-7-[3-[2-(hydroxy)ethyl]-7-oxabicyclo[2.2.1]hept-2-yl]heptanoic acid, methyl ester for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 26

[1β,2α(5Z),3α,4β]-7-[3-[2-(Benzyloxy)ethyl]-7-oxabicyclo[2.2.1]hept-2-yl]-5-heptenoic acid Following the procedure of Example 20 except substituting benzyl methanesulfonate for n-hexyl methanesulfonate, the title compound is obtained.

EXAMPLE 27

[1β,2α(5Z),3β,4β]-7-[3-[2-(Benzyloxy)ethyl]-7-oxabicyclo[2.2.1]hept-2-yl]-5-heptenoic acid Following the proedure of Example 21 except substituting benzyl methanesulfonate for n-hexyl methanesulfonate, the title compound is obtained.

EXAMPLE 28

[1β,2α(5Z),3α,4β]-7-[3-[2-(Cyclopentyloxy)ethyl]-7-oxabicyclo[2.2.1]hept-2-yl]-5-heptenoic acid Following the procedure of Example 20 except substituting cyclopentyl methanesulfonate for n-hexyl methanesulfonate, the title compound is obtained.

EXAMPLE 29

[1β,2α(5Z),3α,4β]-7-[3-[2-(Cyclohexyloxy)ethyl]-7-oxabicyclo[2.2.1]hept-2-yl]-5-heptenoic acid Following the procedure of Example 20 except substituting cyclohexyl methanesulfonate for n-hexyl methanesulfonate, the title compound is obtained.

EXAMPLE 30

[1β,2α(5Z),3α,4β]-7-[3-[4-(Hexyloxy)butyl]-7-oxabicyclo[2.2.1]hept-2-yl]-5-heptenoic acid

A.

[1β,2α(5Z),3α,4β]-7-[3-(3-Oxo)propyl-7-oxabicyclo[2.2.1]hept-2-yl]-5-heptenoic acid, methyl ester Following the procedure of Example 20, part A except substituting [1β,2α(5Z),3α,4β]-7-[3-(2-oxo)-ethyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title A compound is obtained.

B.

[1β,2α(5Z),3α,4β]-7-[3-(4-Oxo)butyl-7-oxabicyclo[2.2.1]hept-2-yl]-5-heptenoic acid, methyl ester Following the procedure of Example 20, part A, except substituting the aldehyde from part A above, for [1β,2α(5Z),3α,4β]-7-[3-formyl-7-oxabicyclo[2.2.1]hept-2-yl]-5-heptenoic acid, methyl ester, the title B aldehyde is obtained.

C.

[1β,2α(5Z),3α,4β]-7-[3-(4-Hydroxybutyl)-7-oxabicyclo[2.2.1]hept-2-yl]-5-heptenoic acid, methyl ester Following the procedure of Example 20, part B, except substituting the title B aldehyde for [1β,2α(5Z),3α,4β]-7-[3-(2-oxo)ethyl-7-oxabicyclo[2.2.1]hept-2-yl]-5-heptenoic acid, methyl ester, the title C alcohol is obtained.

D.

[1β,2α(5Z),3α,4β]-7-[3-[4-(Hexyloxy)butyl]-7-oxabicyclo[2.2.1]hept-2-yl]-5-heptenoic acid Following the procedure of Examples 1 and 2. except substituting the above part C alcohol for the alcohol used in Example 1, the title compound is obtained.

EXAMPLE 31

[1β,2α(5Z),3α,4β]-7-[3-[4-(Cyclohexyloxy)butyl]-7-oxabicyclo[2.2.1]hept-2-yl]-5-heptenoic acid Following the procedure of Example 30 except substituting cyclohexyl methanesulfonate for n-hexyl methanesulfonate, the title compound is obtained.

EXAMPLE 32

[1β,2α(5Z),3α,4β]-7-[3-[4-(Phenyloxy)butyl]-7-oxabicyclo[2.2.1]hept-2-yl]-5-heptenoic acid Following the procedure of Example 11 except substituting [1β,2α(5Z),3α,4β]-7-[3-(4-hydroxybutyl)-7-oxabicyclo[2.2.1]hept-2-yl]-5-heptenoic acid, methyl ester for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 33

[1β,2α(5Z),3α,4β]-7-[3-[4-(Benzyloxy)butyl]-7-oxabicyclo[2.2.1]hept-2-yl]-5-heptenoic acid Following the procedure of Example 30 except substituting benzyl methanesulfonate for n-hexyl methanesulfonate, the title compound is obtained.

EXAMPLE 34

Tris(hydromethyl)aminomethane salt of [1β,2α(5Z),3α,4β]-7-[3-[(Hexyloxy)methyl]-7-oxabicyclo[2.2.1]hept-2-yl]-5-heptenoic acid A solution of the compound formed in Example 2 in methanol is treated with an equivalent amount of tris(hydromethyl)aminomethane. The solvent is removed by evaporation to yield the title compound.

EXAMPLE 35

1β,2α(5Z),3α,4β]-7-[3-[2-(Pentyloxy)ethyl]-7-oxabicyclo[2.2.1]hept-2-yl]-5-heptenoic acid

A.

[1β,2α(5Z),3α,4β]-7-[3-[2-(Pentyloxy)ethyl]-7-oxabicyclo[2.2.1]hept-2-yl]-5-heptenoic acid, pentyl ester A mixture of powdered KOH (0.36 g) in 15 ml of dry xylene was heated to reflux under argon atmosphere and 8 ml of xylene was removed by distillation. To this mixture was added a solution of 200 mg (0.71 mmol) of Example 20, part B. alcohol methyl ester in 17 ml of dry xylene. The volume of the reaction mixture was reduced 15 ml by distillative removal of xylene. To the reaction mixture was then added a solution of 0.5 g (3.55 mmol) pentylmesylate in 10 ml of dry xylene. This mixture was refluxed for 2 hours and 30 minutes. The cooled reaction mixture was diluted with 50 ml of saturated $NaHCO_3$ solution and extracted with $CH_2Cl_2$ (3×60 ml). The combined $CH_2Cl_2$ extracts were dried ($MgSO_4$), filtered and concentrated in vacuo. Purification was effected by flash chromatography on 33 g of silica gel 60 using hexane:ether (5:1) as eluant. This gave 238 mg of title pentyl ester (83%) as a colorless oil. TLC: silica gel, hexane:ether (1:1).

B.

[1β,2α(5Z),3α,4β]-7-[3-[2-(Pentyloxy)ethyl]-7-oxabicyclo[2.2.1]hept-2-yl]-5-heptenoic acid To a stirred solution of 238 mg (0.58 mmol) of pentyl ester from Part A, 26 ml of distilled THF, 2.1 ml of $CH_3OH$ and 3.4 ml of $H_2O$ under argon was added 6.4 ml of 1N aqueous lithium hydroxide solution. This mixture was purged with argon vigorously for 30 minutes and stirred at room temperature for 7 hours. The reaction mixture was acidified to pH 3 by the addition of 1N aqueous HCl solution. The resulting solution was poured into 50 ml of saturated NaCl solution and was saturated with solid NaCl. The aqueous layer was extracted with EtOAc (4×60 ml). The combined EtOAc extracts were dried ($MgSO_4$), filtered and concentrated in vacuo. This was chromatographed on 24 g of silica gel 60 using 3% $CH_3OH$ in $CH_2Cl_2$ as eluant to give 181 mg (92%) of title pure acid, TLC: silica gel, 4% $CH_3OH/CH_2Cl_2$, $R_f$=0.30, vanillin.

Anal. Calcd for $C_{20}H_{34}O_4$: C, 70.97; H, 10.12 $C_{20}H_{34}O_4$ 0.22 $H_2O$: C, 70.16; H, 10.14; Found: C, 70.16; H, 9.87.

EXAMPLE 36

[1β,2α(5Z),3α,4β]-7-[(3-Phenylpropoxy)methyl]-7-oxabicyclo[2.2.1]hept-2-yl]-5-heptenoic acid

A.

[1β,2α(5Z),3α,4β]-7-[(3-Phenylpropoxy)methyl]-7-oxabicyclo[2.2.1]hept-2-yl]-5-heptenoic acid, phenylpropyl ester A mixture of powdered KOH (0.59 g) in 16 ml of dry xylene was heated to reflux under argon atmosphere and 9 ml of xylene was removed by distillation. To this mixture was added a solution of 410 mg (1.53 mmol) of Example 1, part A, alcohol methyl ester in 10 ml of dry xylene. The volume of the reaction mixture was reduced 6 ml by distillative removal of xylene. To the reaction mixture was then added a solution of 1.66 g (7.58 mmol) of 3-phenylpropylmesylate in 36 ml of dry xylene. This mixture was refluxed for 1 hour. The cooled reaction mixture was diluted with 50 ml of saturated $NaHCO_3$ solution and extracted with $CH_2Cl_2$ (3×50 ml). The combined $CH_2Cl_2$ extracts were dried ($MgSO_4$), filtered, and concentrated in vacuo. Purification was effected by flash chromatography on 40 g of silica gel 60 using hexane:ether (3:1) as eluant. This gave 0.61 g of title phenylpropyl ester (81%) as a colorless oil. TLC: silica gel, 2% $CH_3OH/CH_2Cl_2$, $R_f$: 60, iodine.

B.

[1β,2α(5Z),3α,4β]-7-[(3-Phenylpropoxy)methyl]-7-oxabicyclo[2.2.1]hept-2-yl]-5-heptenoic acid To a stirred solution of 610 mg (1.24 mmole) of title A phenylpropyl ester, 55 ml of distilled THF, 4.40 ml of $CH_3OH$ and 7.30 ml of $H_2O$ under argon was added 13.7 ml of 1N aqueous lithium hydroxide solution. This mixture was purged with argon vigorously for 30 minutes and stirred at room temperature for 14 hours. The reaction mixture was diluted with 100 ml of 0.1N aqueous lithium hydroxide solution and washed once with 100 ml of hexane. The reaction mixture was acidified to pH 3 by the addition of 1N aqueous HCl solution and was poured into 100 ml of saturated NaCl solution. The resulting mixture was saturated with solid NaCl and extracted with EtOAc (4×150 ml). The combined EtOAc extracts were dried ($MgSO_4$), filtered and concentrated in vacuo. This was chromatographed on 44 g of silica gel 60 using 4% $CH_3OH$ in $CH_2Cl_2$ as eluant to give 380 mg (82%) of pure title acid. TLC: silica gel, 4% $CH_3OH/CH_2Cl_2$, $R_f$=0.30, iodine.

Anal Calcd for $C_{23}H_{32}O_4$: C, 74.16; H, 8.66 $C_{23}H_{32}O_4$ 0.35 $H_2O$: C, 72.94; H, 8.70; Found: C, 72.94; H, 8.49.

EXAMPLE 37

[1β,2α(5Z),3α,4β]-7-[3-[(Octyloxy)methyl]-7-oxabicyclo[2.2.1]hept-2-yl]-5-heptenoic acid

A.

[1β,2α(5Z),3α,4β]-7-[3-[(Octyloxy)methyl]-7-oxabicyclo[2.2.1]hept-2-yl]-5-heptenoic acid, octyl ester To a stirred solution of 508 mg (1.89 mmol) of Example 1, Part A, ester alcohol in 2.69 ml THF was added in order 2.69 ml (15.6 mmol) of n-octyl bromide, 642 mg (1.89 mmol) of tetrabutylammonium hydrogen sulfate and 2.69 ml of 50% aqueous sodium hydroxide solution. This mixture was stirred at room temperature in darkness for 19 hours. The reaction mixture was poured into 25 ml of saturated sodium bicarbonate solution and extracted with four 25 ml portions of CH$_2$Cl$_2$. The combined CH$_2$Cl$_2$ extracts were dried (MgSO$_4$), filtered, and concentrated in vacuo. Purification was effected by flash chromatography on 39.6 g of silica gel 60 using hexane:ether (3:1) as eluant to give 333 mg (37%) of octyl ester and 250 mg of a mixed band of octyl ester and corresponding methyl ester. TLC: silica gel, 3% CH$_3$OH/CH$_2$Cl$_2$, R$_f$: octyl ester, 0.85; methyl ester, 0.80, iodine.

B.

[1β,2α(5Z),3α,4β]-7-[3-[(Octyloxy)methyl]-7-oxabicyclo[2.2.1]hept-2-yl]-5-heptenoic acid To a stirred solution of 333 mg (0.70 mmol) of Part A octyl ester in 31 ml of distilled THF, 2.50 ml of CH$_3$OH and 4.1 ml of H$_2$O under argon was added 7.70 ml of 1N aqueous lithium hydroxide solution. This mixture was purged with argon vigorously for 20 minutes and stirred at room temperature for 16 hours and 30 minutes. The mixture of octyl ester and corresponding methyl ester was hydrolyzed in the exact same manner. To a stirred solution of this mixture (250 mg) in 29 ml of distilled THF, 2.40 ml of CH$_3$OH and 3.9 ml of H$_2$O, was added 7.30 ml of 1N aqueous lithium hydroxide. This mixture was purged with argon vigorously for 20 minutes and stirred at room temperature for 16 hours and 30 minutes.

These 2 reaction mixtures were combined and diluted with a solution of 120 ml of 0.1N aqueous lithium hydroxide solution and 50 ml of H$_2$O. The resulting mixture was extracted once with 220 ml of hexane. The aqueous layer was acidified to pH 3 by the addition of 1N aqueous HCl solution saturated with solid NaCl, and extracted with EtOAc (4×150 ml). The hexane extract and EtOAc extracts (hexane extract contained the desired acid) were combined, dried (MgSO$_4$), filtered and concentrated in vacuo to give 0.53 g of crude product. This was chromatographed on 48 g of silica gel 60 using 3% CH$_3$OH in CH$_2$Cl$_2$ to give 222 mg (45%) of desired title acid. TLC: silica gel, 4% CH$_3$OH/CH$_2$Cl$_2$, R$_f$=0.40, vanillin Anal. Calcd for C$_{22}$H$_{38}$O$_4$: C, 72.09; H, 10.45; C$_{22}$H$_{38}$O$_4$ 0.24 H$_2$O: C, 71.25; H, 10.45; Found: C, 71.25; H, 10.20.

EXAMPLE 38

[1β,2α(5Z),3α,4β]-7-[3-(Cyclohexylmethoxy)methyl]-7-oxabicyclo[2.2.1]hept-2-yl]-5-heptenoic acid

A.

[1β,2α(5Z),3α,4β]-7-[3-(Cyclohexylmethoxy)methyl]-7-oxabicyclo[2.2.1]hept-2-yl]-5-heptenoic acid, cyclohexylmethyl ester A mixture of powdered KOH (0.56 g) in 15 ml of dry xylene was heated to reflux under argon atmosphere and 7 ml of xylene was removed by distillation. To this mixture was added a solution of 300 mg (1.12 mmol) of Example 1, Part A, alcohol methyl ester in 10 ml of dry xylene. The volume of the reaction mixture was reduced to 11 ml by distillative removal of xylene. To the reaction mixture was then added a solution of 2.47 g (12.9 mmol) cyclohexylmethylmesylate in 10 ml of dry xylene. This mixture was refluxed for 5 hours. The cooled reaction mixture was diluted with 50 ml of saturated NaHCO$_3$ solution and extracted with CH$_2$Cl$_2$ (3×50 ml). The combined CH$_2$Cl$_2$ extracts were dried (MgSO$_4$), filtered and concentrated in vacuo. Purification was affected by flash chromatography on 35 g of silica gel 60 using 1% CH$_3$OH in CH$_2$Cl$_2$ eluant. This gave 0.46 g of title hexyl ester (93%) as a colorless oil. TLC: silica gel, 2% CH$_3$OH/CH$_2$Cl$_2$, R$_f$=0.80, iodine.

B.

[1β,2α(5Z),3α,4β]-7-[3-(Cyclohexylmethoxy)methyl]-7-oxabicyclo[2.2.1]hept-2-yl]-5-heptenoic acid To a stirred solution of 460 mg (1.03 mmol) of Part A cyclohexylmethyl ester, 45 ml of distilled THF, 3.80 ml of CH$_3$OH and 6.10 ml of H$_2$O under argon was added 11.4 ml of 1N aqueous lithium hydroxide solution. This mixture was purged with argon vigorously for 20 minutes and stirred at room temperature for 16 hours. The reaction mixture was diluted with 83 ml of 0.1N aqueous lithium hydroxide solution and washed once with 83 ml of hexane. The aqueous layer was acidified to pH 3 by the addition of 1N aqueous HCl solution and saturated with solid NaCl. The resulting aqueous layer was extracted with EtOAc (4×120 ml). The combined EtOAc extracts were dried (MgSO$_4$), filtered and concentrated in vacuo to give 0.32 g of crude product. This was chromatographed on 34.6 g of silica gel 60 using 3% CH$_3$OH in CH$_2$Cl$_2$ as eluant to give 278 mg (77%) of pure title acid. TLC=silica gel, 4% CH$_3$OH/CH$_2$Cl$_2$, R$_f$=0.28, iodine.

Anal. Calcd for C$_{21}$H$_{34}$O$_4$: C, 71.96; H, 9.78; C$_{21}$H$_{34}$O$_4$ 0.31 H$_2$O: C, 70.84, H, 9.80; Found: C, 70.84; H, 9.68.

EXAMPLE 39

[1β,2α(Z),3β,4β]-7-[3-[(Hexyloxy)methyl]-7-oxabicyclo[2.2.1]hept-2-yl]-5-heptenoic acid

A.

[1β,2α(Z),3β,4β]-7-[3-(Formyl-7-oxabicyclo[2.2.1]hept-2-yl]-5-heptenoic acid, methyl ester To a stirred solution of 1 g of [1β,2α(Z),3α,4β]-7-[3-(formyl)-7-oxabicyclo[2.2.1]hept-2-yl]-5-heptenoic acid, methyl ester (prepared as described in U.S. Pat. No. 4,143,054) in 40 ml of methanol is added 15 mg of sodium methoxide. The resultant solution is stirred for 20 hours at 23° C. under an argon atmosphere. The volume of the reaction mixture is then reduced to 4 ml, diluted with 20 ml of EtOAc, and is washed with saturated NaHCO$_3$ and brine. The EtOAc layer is then dried over MgSO$_4$, filtered, and concentrated in vacuo to afford the title aldehyde.

B.

[1β,2α(Z),3β,4β]-7-[3-(Hydroxymethyl)-7-oxabicyclo[2.2.1]hept-2-yl]-5-heptenoic acid, methyl ester A solution of 266 mg (1 mmol) of Part A [1β,2α(Z),3β,4β]-7-[3-formyl-7-oxabicyclo[2.2.1]hept-2-yl]-5-heptenoic acid, methyl ester and 398 mg of CeCl$_3$.7.6H$_2$O (1.04 mmol) in 16 ml of methanol is cooled to 0° C. To this stirred solution is added 40 mg of NaBH$_4$ (1.04 mmol) in one portion. After stirring for 20 minutes, the reaction mixture is poured into 70 ml of activated NH$_4$Cl solution and is extracted with ethyl acetate (5×40 ml). The combined ethyl acetate extracts are dried over MgSO$_4$, filtered and concentrated in vacuo to give the title alcohol.

C.

[1β,2α(Z),3β,4β]-7-[3-[(Hexyloxy)methyl]-7-oxabicyclo[2.2.1]hept-2-yl]-5-heptenoic acid A mixture of powdered KOH (0.40 g) in 14 ml of dry xylene was heated to reflux under argon atmosphere and 7 ml of xylene was removed by distillation. To this mixture was added a solution of 212 mg (0.79 mmol) of [1β,2α(5Z),3β,4β]-7-[3-[(hydroxymethyl]-7-oxabicyclo[2.2.1]hept-2-yl]-5-heptenoic acid, methyl ester, prepared as described in Part B, in 8 ml of dry xylene. The volume of the reaction mixture was reduced 5 ml by distillative removal of xylene. To the reaction mixture was then added a solution of 0.71 g (3.96 mmol) hexylmesylate in 8 ml of dry xylene. The mixture was refluxed for 2 hours. The cooled reaction mixture was diluted with 40 ml of saturated $NaHCO_3$ solution and extracted with EtOAc (3×70 ml). The combined EtOAc extracts were dried ($MgSO_4$), filtered and concentrated in vacuo. Purification was effected by flash chromatography on 26.4 g of silica gel 60 using 2% $CH_3OH$ in $CH_2Cl_2$ as eluant. This gave 220 mg of pure title acid (82%) as a colorless oil. TLC: silica gel, 1:1 hexane-ether, $R_f$=0.30, iodine.

Anal Calcd for $C_{20}H_{34}O_4$: C, 70.97; H, 10.12; Found: C, 70.93; H, 10.33.

EXAMPLE 40

[1β,2β(Z),3α,4β]-7-[3-[(Hexyloxy)methyl]-7-oxabicyclo[2.2.1]hept-2-yl]-5-heptenoic acid

A.

[1β,2β(5Z),3α,4β]-7-[3-Formyl-7-oxabicyclo[2.2.1]hept-2-yl]-5-heptenoic acid, methyl ester A solution of pyridine (8.7 ml) in dichloromethane (200 ml) was treated portionwise with chromium trioxide (5.38 g) with vigorous stirring. After addition was complete, the mixture was stirred at room temperature for 20 minutes, then treated with celite (8 g), then [1β,2β(5Z),3β,4β]-7-[3-(hydroxymethyl)-7-oxabicyclo[2.2.1]-hept-2-yl]-5-heptenoic acid, methyl ester prepared as described in U.S. Pat. No. 4,143,054 (2.58 g, 0.0096 moles) in dichloromethane (10 ml). The reaction mixture was stirred at room temperature for 20 minutes, then filtered through celite. The filtrate was washed with 5% sodium bicarbonate (2×100 ml), 10% hydrochloric acid (2×100 ml) and again with 5% sodium bicarbonate (2×100 ml). The dichloromethane solution was dried over magnesium sulfate and concentrated in vacuo. The residue was chromatographed on silicar CC-7 (200 ml) eluting with (1) dichloromethane and (2) diethyl ether to yield 2 g of aldehyde. NMR (C-13 & proton) indicated the product to be a mixture of isomers (90% cis-endo and 10% trans-aldehyde). Drying in vacuo at room temperature for any extended period of time caused decomposition as evidenced by thin layer chromatography. TLC: silica gel; benzene/EtOAc (4:1) $R_f$=0.5; visualized with vanillin spray and heat.

B.

[1β,2β(Z),3α,4β]-7-[3-(Hydroxymethyl)-7-oxabicyclo[2.2.1]hept-2-yl]-5-heptenoic acid, methyl ester A solution of 266 mg (1 mmol) of the trans-aldehyde from Part A, namely, [1β,2β(Z),3α,4β]-7-[3-formyl-7-oxabicyclo]2.2.1]hept-2-yl]-5-heptenoic acid, methyl ester and 398 mg of $CeCl_3 \cdot 6H_2O$ (1.04 mmol) in 16 ml of methanol is cooled to 0° C. To this stirred solution is added 40 mg of $NaBH_4$ (1.04 mmol) in one portion. After stirring for 20 minutes, the reaction mixture is poured into 70 ml of activated $NH_4Cl$ solution and is extracted with ethyl acetate (5×40 ml). The combined ethyl acetate extracts are dried over $MgSO_4$, filtered and concentrated in vacuo to give the title alcohol.

C.

[1β,2β(Z),3α,4β]-7-[3-[(Hexyloxy)methyl]-7-oxabicyclo[2.2.1]hept-2-yl]-5-heptenoic acid A mixture of powdered KOH (0.62 g) in 18 ml of dry xylene was heated to reflux under argon atmosphere and 9 ml of xylene was removed by distillation. To this mixture was added a solution of 330 mg (1.23 mmol) of title A alcohol methyl ester in 12 ml of dry xylene. The volume of the reaction mixture was reduced 6 ml of distillative removal of xylene. To the reaction mixture was then added a solution of 1.11 g (6.16 mmol) of hexylmesylate in 10 ml of dry xylene. The mixture was refluxed for one hour and forty-five minutes. The cooled reaction mixture was diluted with 50 ml of saturated $NH_4Cl$ solution and extracted once with 50 ml of EtOAc. The aqueous layer was separated, acidified to pH 2 by the addition of 1N aqueous HCl solution and extracted with EtOAc (3×50 ml). The combined EtOAc extracts were dried ($MgSO_4$), filtered and concentrated in vacuo. Purification was effected by flash chromatography on 31 g of silica gel 60 using 2% $CH_3OH$ in $CH_2Cl_2$ as eluant. This gave 270 mg of pure title acid (65%) as a colorless oil. TLC=silica gel, 2:1 ether-hexane, $R_f$=0.40, iodine.

Anal Calcd for $C_{20}H_{34}O_4$: C, 70.97; H, 10.12; Found: C, 71.14; H, 9.84.

EXAMPLE 41

[1R-[1α,2β(Z),3β,4α]]-7-[3-[(Hexyloxy)methyl]-7-oxabicyclo[2.2.1]hept-2-yl]-5-heptenoic acid, hexyl ester

A.

[3aR-[1-(1R,2S,5R),3aα,4α,7α,7aα]]Octahydro-1-[[5-methyl-2-(1-methylethyl)cyclohexyl]oxy]-4,7-epoxyisobenzofuran A solution of (exo)-octanhydro-4,7-epoxyisobenzofuran-1-ol prepared as described in U.S. Pat. No. 4,143,054 (21 g, 0.13 mole), levo-methanol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,7aα]]-octahydro-1-[[5-methyl-2-(1-methylethyl)cyclohexyl]oxy]-4,7-epoxyisobenzofuran, m.p. 109°-111° C.

B.

[3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f$=0.25; vanillin spray and heat.

C.
[3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[\alpha]_D$= −44°; $[\alpha]^{Hg}_{365}$= −122°; c=10 mg/ml MeOH

TLC: silica gel; ethyl acetate/dichloromethane (1:1), $R_f$=0.2; vanillin spray and heat.

D.
[1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title D compound, b.p. 90° C./0.01 mm.

$[\alpha]_D$= +44°; $[\alpha]^{Hg}_{365}$= +138°; c=11 mg/ml MeOH

TLC: silica gel; ethyl acetate/dichloromethane (1:1); $R_f$=0.2; vanillin spray and heat.

E.
[4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°–105° C.

$[\alpha]_D$= +27.2°; $[\alpha]^{Hg}_{365}$=0; c=7.9 mg/ml MeOH

F.
[1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D$= +11.2°; $[\alpha]^{Hg}_{365}$=0; c=16.9 mg/ml MeOH

TLC: silica gel; ether; $R_f$=0.4; vanillin spray and heat.

G.
[1R-[1α,2β(Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was heated to reflux under argon atmosphere and 12 ml of xylene was removed by distillation. To this mixture was added a solution of 500 mg (1.86 mmol) of title F alcohol methyl ester in 16 ml of dry xylene. The volume of the reaction mixture was reduced 12 ml by distillative removal of xylene. To the reaction mixture was then added a solution of 1.68 g (9.30 mmol) hexylmesylate in 16 ml of dry xylene. This mixture was refluxed for 1 hour and 15 minutes. The cooled reaction mixture was diluted with 100 ml of saturated $NaHCO_3$ solution and extracted with $CH_2Cl_2$ (3×100 ml). The combined $CH_2Cl_2$ extracts were washed with brine (1×200 ml), dried ($MgSO_4$), filtered and concentrated in vacuo. Purification was effected by flash chromatography on 46 g of silica gel 60 using hexane:ethane (5:1) as eluant. This gave 0.62 g of title hexyl ester (79%) as a colorless oil. TLC: silica gel, 2% $CH_3OH/CH_2Cl_2$, $R_f$: 0.80, iodine.

EXAMPLE 42

1R-[1α,2β(Z),3β,4α]]-7-[3-[(Hexyloxy)methyl]-7-oxabicyclo[2.2.1]hept-2-yl]-5-heptenoic acid To a stirred solution of 517 mg (1.12 mmol) of Example 41 hexyl ester, 55 ml of distilled THF, 4.40 ml of CH$_3$OH and 7.20 ml of H$_2$O under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4×150 ml). The combined EtOAc extracts were dried (MgSO$_4$), filtered and concentrated in vacuo. This was chromatographed on 40 g of silica gel 60 using 4% CH$_3$OH in CH$_2$Cl$_2$ as eluant to give the desired product contaminated with a small amount of hexyl alcohol. The product was pumped under high vacuum for ~60 hours at room temperature to give 350 mg (85%) of pure title acid. TLC: silica gel. 4% CH$_3$OH/CH$_2$Cl$_2$, R$_f$=0.42, iodine.

[α]$_D$=+5.2° (CHCl$_3$)

Anal Calcd for C$_{20}$H$_{34}$O$_4$: C, 70.92; H, 10.12; Found: C, 70.66; H, 9.99.

EXAMPLE 43

[1R-[1α,2β(Z),3β,4α]]-7-[3-[(Hexyloxy)methyl]-7-oxabicyclo[2.2.1]hept-2-yl]-5-heptenoic acid, 2-amino-2-(hydroxymethyl)-1,3-propanediol salt (1:1)

A solution of 2.88 g (23.8 mmol) of tris-(hydroxymethyl)-aminomethane in 150 ml of MeOH was added to a solution of 8.05 g (23.8 mmol) of Example 42 acid in 50 ml of MeOH. The resulting solution was concentrated in vacuo to afford a taffy-like oil. On further drying in vacuo the oil crystallized to give 11.0 g of title salt (100%), m.p. 68.5°–70° C.

Anal Calcd for C$_{24}$H$_{45}$O$_7$N: C, 62.72; H, 9.87; N, 3.04; Found: C, 62.71; H, 9.80; N, 3.10.

EXAMPLE 44

[1α,2β(Z),3β,4α]-7-[3-[[(2-Methylhexyl)oxy]methyl]-7-oxabicyclo[2.2.1]hept-2-yl]-5-heptenoic acid, methyl ester A mixture of 0.67 g (120 mmol) of powdered KOH in 20 ml of dry xylene was heated to reflux and ~10 ml of xylene was removed by distillation. To this stirred mixture was added a solution of 400 mg (1.49 mmol) of [1α,2β(Z),3β,4α]-7-[3-(hydroxymethyl)-7-oxabicyclo[2.2.1]hept-2-yl]-5-heptenoic acid, methyl ester prepared as described in U.S. Pat. No. 4,143,054 in 6 ml of xylene. Approximately 10 ml of xylene was removed by distillation to afford a clear solution with a gummy precipitate adhering to the magnetic stirring bar. To this mixture was added a solution of 1.45 g (7.5 mmol) of crude 2-methyl-hexylmesylate in 4 ml of xylene. This caused the gummy precipitate to break up to form a somewhat gelatinous reaction mixture. The mixture was refluxed for 2¼ hour. The cooled reaction mixture was partitioned between 20 ml each saturated NH$_4$Cl and EtOAc. The aqueous layer was acidified to pH=3.5 and then extracted with three 20 ml portions of EtOAc. The combined EtOAc extracts were dried (MgSO$_4$), filtered and concentrated in vacuo to give the crude product which was treated with excess ethereal CH$_2$N$_2$. The crude product was purified by flash chromatography on 35 g of silica gel using 4:1 hexane/ether as eluant. Fractions 15–20 were concentrated to give 320 mg of title ether (58%). Fractions 23–27 afforded 100 mg of the n-hexyl ether related to title ether (19%). (Apparently, the commercial 2-methyl-hexanoic acid which was the precursor to the mesylate employed was contaminated with ~10% hexanoic acid) and fractions 21–22 gave 70 mg (13%) of a mixture of these two ethers.

EXAMPLE 45

[1α,2β(Z),3β,4α]-7-[3-[[(2-Methylhexyl)oxy]methy]-7-oxabicyclo[2.2.1]hept-2-yl]-5-heptenoic acid A solution of 310 mg (0.85 mmol) of Example 44 ether in 30 ml of distilled THF and 4.1 ml of H$_2$O was purged with a stream of argon for 10 minutes. To this stirred solution was added 7.7 ml of 1N LiOH followed by 3 ml of CH$_3$OH. The resulting mixture was stirred at room temperature for 6 hours. The reaction mixture was partitioned between 70 ml saturated NaCl solution and 50 ml EtOAc. The aqueous layer was acidified to pH=1.0 and extracted with two 50 ml portions of EtOAc. The combined EtOAc extracts were dried over MgSO$_4$, filtered and concentrated in vacuo to the crude product. Flash chromatography on 43 g of silica gel using 2% MeOH/CH$_2$Cl$_2$ as eluant afforded 250 mg of title acid. TLC: 3% CH$_3$OH/CH$_2$Cl$_2$ silica gel; R$_f$=0.17; iodine.

Anal Calcd for C$_{21}$H$_{16}$O$_4$: C, 71.55; H, 8.30; Found: C, 71.59; H, 8.32.

EXAMPLES 46 AND 47

[1β,2α(Z),3α,4β]-7-[3-[1-(Hexyloxy)ethyl]-7-oxabicyclo[2.2.1]hept-2-yl]-5-heptenoic acid, hexyl ester

A.

[1β,2α(Z),3α,4β]-7-[3-[1-(hydroxy)ethyl]-7-oxabicyclo[2.2.1]hept-2-yl]-5-heptenoic acid, methyl ester To a stirred solution of 1.31 g (4.91 mmol) of [1β,2α(Z),3α,4β]-7-(3-formyl)-7-oxabicyclo[2.2.1]hept-5-en-2-yl]-5-heptenoic acid, methyl ester, prepared as described in U.S. Pat. No. 4,143,054 at −78° C. under argon atmosphere was added 1.64 ml of 3M CH$_3$MgBr dropwise in a period of 10 minutes. The reaction mixture was stirred for 5 minutes and the acetone-dry ice bath was removed. The reaction mixture was stirred for another 12 minutes and quenched with 1 ml of CH$_3$OH. The reaction mixture was then poured into 20 ml of saturated NH$_4$Cl solution and diluted with a solution of 40 ml of H$_2$O and 40 ml of saturated NH$_4$Cl solution. The aqueous layer was extracted with ether (3×100 ml). The combined ether extracts were dried (MgSO$_4$), filtered and concentrated in vacuo to give 1.58 g of the title alcohol methyl ester which was used as is without further purification. TLC: silica gel, 4% CH$_3$OH/CH$_2$Cl$_2$, R$_f$=0.25, iodine.

B.

[1β,2α(Z),3α,4β]-7-[3-[1-(Hexyloxy)ethyl]-7-oxabicyclo[2.2.1]hept-2-yl]-5-heptenoic acid, hexyl ester (fast moving isomer) and

C.

[1β,2α(Z),3α,4β]-7-[3-[1-(Hexyloxy)ethyl]-7-oxabicyclo[2.2.1]hept-2-yl]-5-heptenoic acid, hexyl ester (slow moving isomer)

A mixture of powdered KOH (2.57 g) in 100 ml of dry xylene was heated to reflux under argon atmosphere and 50 ml of xylene was removed by distillation. To this mixture was added a solution of 1.25 g (4.43 mmol) of title A alcohol methyl ester in 100 ml of dry xylene. The volume of the reaction mixture was reduced 50 ml by distillative removal of xylene. To the reaction mixture was then added a solution of 4.63 g (25.7 mmol) of hexylmesylate in 50 ml of dry xylene. This mixture was refluxed for 85 minutes at which time an additional 0.42 g of hexylmesylate was added. This mixture was refluxed for an additional 3 hours. The cooled reaction mixture was diluted with 250 ml of saturated NaCl solution and extracted with EtOAc (3×200 ml). The combined EtOAc extracts were dried (MgSO$_4$), filtered and concentrated in vacuo. The residue was treated with 120 ml of diazomethane at 0° C. and then allowed to warm up to room temperature for 2 hours. The solvent and excess diazomethane was removed by concentration in vacuo. Purification was effected by flash chromatography on 155 g of silica gel 60 using 4:1 hexane-ether as eluant. This gave 570 mg of fast moving isomer of hexyl ester (title B) (29%), 260 mg of impure slow moving isomer of hexyl ester (title C) (13%), 160 mg of mixture of F.M.I. and S.M.I. (9%), and 220 mg of recovered alcohol hexyl ester.

TLC: silica gel, 2:1 hexane-ether; $R_f$=fast moving isomer, 0.70; slow moving isomer, 0.65, iodine

EXAMPLE 48

[1β,2α(Z),3α,4β]-7-[3-[1-(Hexyloxy)ethyl]-7-oxabicyclo[2.2.1]hept-2-yl]-5-heptenoic acid (fast moving isomer)

To a stirred solution of 570 mg (1.31 mmol) of Example 46 title B (fast moving isomer) ester, 58 ml of distilled THF, 4.8 ml of CH$_3$OH and 7.9 ml of H$_2$O under argon was added 14.8 ml of 1N aqueous lithium hydroxide solution. This mixture was purged with argon vigorously for 30 minutes and stirred at room temperature for 7 hours. The reaction mixture was acidified to pH 2 by the addition of 1N aqueous HCl solution. The resulting solution was poured into 120 ml of saturated NaCl solution and was saturated with solid NaCl. The aqueous layer was extracted with EtOAc (4×100 ml). The combined EtOAc extracts were dried (MgSO$_4$), filtered and concentrated in vacuo. This was chromatographed on 40 g of silica gel 60 using 3% CH$_3$OH in CH$_2$Cl$_2$ as eluant to give 388 mg (85%) of pure title acid.

TLC: Silica gel, 4% CH$_3$OH/CH$_2$Cl$_2$, $R_f$=0.4, iodine.

Anal Calcd for C$_{21}$H$_{36}$O$_4$: C, 71.55; H, 10.29; Found: C, 71.36; H, 10.39.

EXAMPLE 49

[1α,2α(Z),3α,4α]-7-[3-[(Hexyloxy)methyl]-7-oxabicyclo[2.2.1]hept-2-yl]-5-heptenoic acid, hexyl ester A mixture of 900 mg (16.1 mmol) of powdered KOH in 26 ml of xylene was heated to reflux and 13 ml was removed by distillation. To this hot solution was added a solution of 480 mg (1.79 mmol) of [1α,2α(Z),3α,4α]-7-(3-hydroxymethyl)-7-oxabicyclo[2.2.1]hept-2-yl]-5-heptenoic acid, methyl ester (prepared as described in U.S. Pat. No. 4,143,054) in 17 ml xylene. The volume was reduced 10 ml by distillative removal of xylene. Then a solution of 2.00 g (11.1 mmol) of n-hexyl mesylate in 15 ml of xylene was added and an additional 6 ml of xylene was removed by distillation. This mixture was refluxed for an additional 30 minutes and then allowed to cool to room temperature.

The cooled reaction mixture was partitioned between 40 ml each of saturated NH$_4$Cl and EtOAc. The aqueous layer was acidified to pH 2 with 1N HCl. The aqueous layer was extracted with two 40 ml portions of EtOAc. The combined EtOAc layers were dried over MgSO$_4$, filtered, and concentrated in vacuo to afford the crude product. Purification was effected by chromatography on 42 g of silica gel using 4:1 hexane-ether as eluant. This gave 460 mg (61%) of pure title hexyl ester and 70 mg (15%) of slightly impure title hexyl ester.

EXAMPLE 50

[1α,2α(Z),3α,4α]-7-[3-[(Hexyloxy)methyl]-7-oxabicyclo[2.2.1]hept-2-yl]-5-heptenoic acid A solution of 460 mg (1.09 mmol) of Example 49 ester in 3.3 ml of THF was purged with argon. To this stirred solution was added 0.7 ml of H$_2$O and 1.4 ml of 1N LiOH. To the resulting two-phase mixture was added 1.5 ml CH$_3$OH and 1.5 ml THF which afforded a homogeneous mixture. This solution was stirred overnight at room temperature. The reaction mixture was partitioned between 20 ml each of saturated NaCl and EtOAc. The aqueous layer was acidified with 1N HCl to pH=2 and then extracted with two 20 ml portions of EtOAc. The combined EtOAc layers were dried over MgSO$_4$, filtered and concentrated in vacuo to give 400 mg of crude product. Purification was effected by flash chromatography on 30 g of silica gel using 2% MeOH/CH$_2$Cl$_2$ as eluant to afford 294 mg of title acid (80%). TLC silica gel, 4% CH$_3$OH/CH$_2$Cl$_2$, iodine, $R_f$=0.32.

Anal Calcd for C$_{20}$H$_{34}$O$_4$: C, 70.97; H, 10.12; Found: C, 71.10; H, 10.03.

EXAMPLE 51

[1R-[1α,2β,3β,4α]]-7-[3-[(Hexyloxy)methyl]-7-oxabicyclo[2.2.1]hept-2-yl]heptanoic acid To a solution of 120 mg (0.36 mmol) of Example 42 acid in 6 ml of EtOAc under argon was added 24 mg (20% based on weight of Example 42 acid) of 10% Pd/Carbon. The argon was replaced by hydrogen with several vacuum fill cycles. The reaction mixture was stirred at room temperature under a slight positive pressure of hydrogen for 14 hours. The catalyst was filtered off and the solution was concentrated in vacuo to give 110 mg of product. Analysis of the crude product by 270 MHz $^1$H NMR revealed the presence of 5-7% of Example 42 acid. This material was again subjected to the reaction conditions described above to afford 110 mg of title acid. Purification was effected by flash chromatography on 22 grams of silica gel using 2% MeOH/CH$_2$Cl$_2$ as eluant. This afforded 105 mg (87%) of pure title acid.

TLC: silica gel; 8% CH$_3$OH/CH$_2$Cl$_2$, $R_f$=0.74, iodine.

Anal Calcd for C$_{20}$H$_{36}$O$_4$: C, 70.55; H, 10.66; Found: C, 70.30; H, 10.70.

[α]$_D$= −3.1° (c=1.37, CHCl$_3$).

EXAMPLE 52

[1α,2β(Z),3β,4α]-7-[3-[[(1-Methylhexyl)oxy]methyl]-7-oxabicyclo[2.2.1]hept-2-yl]-5-heptenoic acid, 1-methyl hexyl ester A. Fast moving isomer (FMI) and
B. Slow moving isomer (SMI)

A mixture of powdered KOH (1.03 g) in 28 ml of dry xylene was heated to reflux under argon atmosphere and 14 ml of xylene was removed by distillation. To this mixture was added a solution of 550 mg (2.05 mmol) of [1α,2β(Z),3β,4α]-7-[3-(hydroxymethyl)-7-oxabicyclo[2.2.1]hept-2-yl]-5-heptenoic acid, methyl ester, prepared as described in U.S. Pat. No. 4,143,054, in 18 ml of dry xylene. The volume of the reaction mixture was reduced 16 ml distillative removal of xylene. To the reaction mixture was then added a solution of 2.00 g (10.3 mmol) of 2-heptyl mesylate in 15 ml of dry xylene. This mixture was refluxed for 4 hours and 40 minutes. The cooled reaction mixture was diluted with 100 ml of saturated NaCl solution and extracted with EtOAc (4×100 ml). The combined EtOAc extracts were dried (MgSO$_4$), filtered and concentrated in vacuo. The residue was treated with 40 ml of diazomethane solution at room temperature for 1 hour and concentrated in vacuo. This was chromatographed on 88 g of silica gel 60 using 4:1 hexane-ether as eluant to give 40 mg of fast moving isomer of ester of title A, 60 mg (7%) of slow moving isomer of ester of title B, 260 mg of a mixture of FMI and SMI and 300 mg (40%) of the heptyl ester of starting alcohol. The mixture of FMI and SMI ws rechromatographed on 41 g of silica gel 60 using 4:1 hexane-ether as eluant. This gave 60 mg of FMI ester and 190 mg (21%) of a mixture of SMI and FMI. The FMI ester obtained from these 2 columns were combined (100 mg, 11%). TLC: silica gel, 2:1 hexane-ether, R$_f$=FMI, 0.65; SMI, 0.60 iodine.

EXAMPLE 53

[1α,2β(Z),3β,4α]-7-[3-[[(1-Methylhexyl)oxy]methyl]-7-oxabicyclo[2.2.1]hept-2-yl]-5-heptenoic acid (Fast moving isomer)

To a stirred solution of 100 mg (0.22 mmol) of Example 52A ester, 10.2 ml of freshly distilled THF, 0.83 ml of CH$_3$OH and 1.40 ml of H$_2$O under argon was added 2.60 ml of 1N aqueous lithium hydroxide solution. This mixture was purged with argon vigorously for 5 minutes and stirred at room temperature for 4 hours at which time 1 ml of CH$_3$OH was added. The reaction mixture was stirred for another 17 hours and 1 ml of CH$_3$OH was added. The reaction mixture was stirred for 1 more hour and was acidified to pH 3 by the addition of 1N aqueous HCl solution. The resulting solution was poured into 30 ml of saturated NaCl solution and was saturated with solid NaCl. The aqueous layer was extracted with EtOAc (4×50 ml). The combined EtOAc extracts were dried (MgSO$_4$), filtered and concentrated in vacuo. Purification was effected by flash chromatography on 22.4 g of silic gel 60 using 2% CH$_3$OH in CH$_2$Cl$_2$ as eluant. The desired product was collected and pumped under high vacuum at room temperature to give 70 mg (89%) of pure title acid. TLC: silica gel, 4% CH$_3$OH/CH$_2$Cl$_2$, R$_f$=0.47, iodine.

Anal Calcd for C$_{21}$H$_{36}$O$_4$: C, 71.55; H, 10.29; Found: C, 71.73; H, 10.21.

EXAMPLE 54

[1α,2β(Z),3β,4α]-7-[3-[[(1-Methylhexyl)oxy]methyl]-7-oxabicyclo[2.2.1]hept-2-yl]-5-heptenoic acid, methyl ester (Slow moving isomer)

To a stirred solution of 190 mg (0.42 mmol) of a mixture of Example 52B SMI 1-methylhexyl ester and the corresponding FMI ester Example 52A, 19.2 ml of freshly distilled THF, 1.6 ml of CH$_3$OH and 2.6 ml of H$_2$O under argon was added 4.8 ml of 1N aqueous lithium hydroxide solution. This mixture was purged with argon vigorously for 5 minutes and stirred at room temperature for 4 hours at which time 2 ml of CH$_3$OH was added. The mixture was stirred for another 17 hours and 1 ml of CH$_3$OH was added. The reaction mixture was stirred for an additional hour and acidified to pH 3 by the addition of 1N aqueous HCl solution. The resulting solution was poured into 50 ml of saturated NaCl solution and was saturated with solid NaCl. The aqueous layer was extracted with EtOAc (4×60 ml). The combined EtOAc extracts were dried (MgSO$_4$), filtered and concentrated in vacuo. The residue was treated with 30 ml of ethereal CH$_2$N$_2$ solution at room temperature for 3 hours. Concentration of this solution in vacuo gave a colorless oil. This was chromatographed on 24.7 g of silica gel 60 using 4:1 hexane:ether as eluant to give 49 mg (32%) of title slow moving isomer of methyl ester. TLC=silica gel, 2:1 hexane-ether, R$_f$FMI (methyl ester), 0.48; SMI (methyl ester), 0.37 iodine.

EXAMPLE 55

[1α,2β(Z),3β,4α]-7-[3-[[(1-Methylhexyl)oxy]methyl]-7-oxabicyclo[2.2.1]hept-2-yl]-5-heptenoic acid To a stirred solution of 49 mg (0.13 mmol) of Example 54 methyl ester, 7.5 ml of freshly distilled THF and 0.8 ml of H$_2$O under argon was added 1.4 ml of 1N aqueous lithium hydroxide solution. This mixture was purged with argon vigorously for 5 minutes and stirred at room temperature for 6 hours. The reaction mixture was acidified to pH 3 by the addition of 1N aqueous HCl solution and diluted with 15 ml of brine. The resulting mixture was saturated with solid NaCl and extracted with three 40 ml portions of EtOAc. The combined EtOAc extracts were dried (MgSO$_4$), filtered and concentrated in vacuo. Purification was effected by flash chromatography on 15 g of silica gel 60 using 2% CH$_3$OH in CH$_2$Cl$_2$ as eluant. This gave 41 mg (87%) of pure title acid. TLC: silica gel, 4% CH$_3$OH/CH$_2$Cl$_2$. R$_f$=0.47, iodine.

Anal Calcd for C$_{21}$C$_{36}$O$_4$: C, 71.55; H, 10.29; Found: C, 71.22; H, 10.25.

EXAMPLE 56

[1R-[1α,2β(Z),3β,4α]-7-[3-(Methoxymethyl)-7-oxabicyclo[2.2.1]hept-2-yl]-5-heptenoic acid

A.

[1R-[1α,2β(Z),3β,4α]-7-[3-Methoxymethyl)-7-oxabicyclo[2.2.1]hept-2-yl]-5-heptenoic acid, methyl ester A solution of 65 g of crude [1β,2α(Z),3α,4β]-7-[3-(hydroxymethyl)-7-oxabicyclo[2.2.1]hept-2-yl]-5-heptenoic acid in 300 ml of CH$_3$OH was cooled in an ice bath and treated portionwise with excess ethereal CH$_2$N$_2$ solution. After standing for 30 minutes, the reaction mixture was concentrated in vacuo to give the corresponding methyl ester contaminated with a small amount of [1β,2α(Z),3α,4β]-7-[3-(methoxymethyl)-7-oxabicyclo[2.2.1]hept-2-yl]-5-heptenoic acid, methyl ester. This impurity was partially purified by chromatography of the mixture on a Waters Prep 500 ™ chromatograph using hexane/EtOAC (33–60%) mixtures as eluants. Further purification on 140 g of silica gel using 3:1 hexane-ether as eluant afforded 1.4 g of [1β,2α(Z)-,3α,4β]-7-[3-(methoxymethyl)-7-oxabicyclo[2.2.1]hept-2-yl]-5-heptenoic acid, methyl ester.

B.
[1R-[1α,2β(Z),3β,4α]-7-[3-(Methoxymethyl)-7-oxabicyclo[2.2.1]hept-2-yl]-5-heptenoic acid To a stirred solution of 1.4 g of title A ester (4.96 mmol) in 250 ml of THF under argon was added 42 ml of $H_2O$ and 49 ml of 1N LiOH solution. The resulting mixture was purged with argon for 30 minutes, and then stirred at room temperature for 17 hours. The reaction mixture was poured into 250 ml of brine and acidified to pH=3 with 1N HCl. The aqueous layer was saturated with NaCl and extracted with four 250 ml portions of EtOAc. The combined EtOAc layers were dried over $MgSO_4$, filtered and concentrated in vacuo to give the crude product. Chromatography of this material on 71 g of silica gel afforded 1.24 g (93%) of impure title B acid (the impurity was the corresponding acid with one less methylene in the alpha-chain). TLC: silica gel, 4% $CH_3OH/CH_2Cl_2$, $R_f=0.3$, iodine.

C. Amine salt of [1R-[1α,2β(Z),3β,4α]-7-[3-(Methoxymethyl)-7-oxabicyclo[2.2.1]hept-2-yl]-5-heptenoic acid To a freshly prepared solution of 0.7 g adamantylamine (4.63 mmol) in 18 ml EtOAc was added a solution of 1.24 g of title B material (4.63 mmol) in 20 ml EtOAc. A white precipitate formed immediately. After standing overnight at room temperature, the solid was collected and dried in vacuo to afford 1.7 g of title amine-salt (88%).

D.
[1R-[1α,2β(Z),3β,4α]-7-[3-(Methoxymethyl)-7-oxabicyclo[2.2.1]hept-2-yl]-5-heptenoic acid The above title C amine salt in the form of a white solid was dissolved in 20 ml of 1:1 $CH_3CN/H_2O$. After cooling to room temperature, fine clumps of needles began to form. The flask was stored in the refrigerator overnight. The crystals were collected and dried in vacuo to afford 0.8 g of amine salt (47%). A portion (700 mg) of these crystals were partitioned between 10 ml saturated NaCl, 10 ml 1N HCl and 20 ml EtOAc. The aqueous layer was extracted once with 20 ml EtOAc. The combined EtOAc layers were washed with 20 ml of 0.1N HCl, dried over $MgSO_4$, filtered and concentrated in vacuo to afford 0.41 g title acid (92%). Purification was effected by flash chromatography on 30 g silica gel using 2% $MeOH/CH_2Cl_2$ to afford 360 mg of pure title acid. TLC silica gel, 4% $CH_3OH/CH_2Cl_2$, $R_f=0.3$, iodine.

Anal Calcd for $C_{15}H_{24}O_4$: C, 67.14; H, 9.01; Found: C, 67.03; H, 9.14.

$[α]_D = +10.4°$ (C=2.21, $CHCl_3$).

EXAMPLE 57

[1α,2β(5Z),3β,4α]-7-[3-[(Hexyloxy)methyl]-7-oxabicyclo[2.2.1]hept-2-yl]-3,3-dimethyl-5-heptenoic acid, hexyl ester

A. 4-Carboxy-3,3-dimethylbutyl triphenyl phosphonium bromide

A suspension of 5.8 g (0.15 mole) of sodium borohydride in 30 ml of dry tetrahydrofuran was stirred and cooled in an ice bath under nitrogen while 21.32 g (0.15 mole) of 3,3-dimethyl glutaric anhydride in 120 ml of dry tetrahydrofuran was added in 5 minutes. The ice bath was then removed and stirring was continued for 2 hours. Hydrochloric acid (6N, 60 ml) was added cautiously and the mixture was then concentrated in vacuo. Water (300 ml) was added and the mixture was extracted with ethyl ether. The ethyl ether extract was dried over anhydrous $Na_2SO_4$, concentrated in vacuo and distilled (60°, 1 mm Hg) giving 13.1 g (68.2%) of 3,3-dimethyl valerolactone with consistent $^1$H-NMR spectral data. This lactone (5 g, 39.04 mmole) and triphenyl phosphine hydrobromide (13.56 g, 39.04 mmole) were heated neat under nitrogen at 175° (oil bath temperature) for 3.5 hours. The reaction mixture was cooled to room temperature, diluted with 100 ml of water-ethyl acetate (1:1) and the phases were separated. The aqueous phase was washed again with ethyl acetate, treated with charcoal, filtered and lyophilized to yield 12 g (65.2%) of 4-carboxy-3,3-dimethylbutyltriphenylphosphonium bromide with consistent $^1$H-NMR spectral data. This was dried (65°, 0.3 mm Hg, 18 hours) prior to use.

B.
[1α,2β(5Z),3β,4α]-7-[3-(Hydroxymethyl)-7-oxabicyclo[2.2.1]hept-2-yl]-3,3-dimethyl-5-heptenoic acid, methyl ester A slurry of 4-carboxy-3,3-dimethylbutyltriphenylphosphonium bromide (1.414 g, 3.0 mmole) and (exo)octahydro-5,8-epoxy-1H-benzopyran-3-ol (340.4 mg, 2.0 mmole) in 10 ml of dry toluene was chilled to 0° and treated dropwise with a solution of 1.27M potassium t-amylate in toluene (4.7 ml, 5.97 mmole) over 30 minutes. The mixture was then stirred at room temperature overnight. It was then chilled in an ice bath and was treated slowly with glacial acetic acid (0.3 ml) in 2 ml of toluene, diluted with water (5 ml) and acidified with concentrated hydrochloric acid to pH 2.5. The mixture was then diluted with ethyl acetate (20 ml), saturated with sodium chloride and filtered through a bed of HYFLO. The solids were washed with ethyl acetate (2×25 ml). The toluene-ethyl acetate layer was separated and the aqueous layer was extracted with ethyl acetate (3×25 ml). The combined extracts were dried (anhydrous $MgSO_4$) and evaporated in vacuo to give an oil. This was dissolved in 120 ml of dichloromethane-ethyl ether (1:1) and esterified with an ethereal solution of diazomethane. The excess diazomethane was destroyed with acetic acid and the solvent was evaporated in vacuo to give the impure title alcohol methyl ester. This was flash-chromatographed on a 200 g silica gel (LPS-1) column, eluting with ethyl acetate-hexane (1:1) to give 356 mg (60%) of the title homogeneous (tlc) alcohol methyl ester with consistent $^1$H-NMR and $^{13}$C-NMR spectral data.

C.
[1α,2β(5Z),3β,4α]-7-[3-[(Hexyloxy)methyl]-7-oxabicyclo[2.2.1]hept-2-yl]-3,3-dimethyl-5-heptenoic acid, hexyl ester A stirred mixture of powdered KOH (500 mg, 8.9 mmole) in 40 ml of dry xylene was heated to reflux under nitrogen and 20 ml of xylene was removed by distillation. To this was added dropwise a solution of Part B alcohol methyl ester (350 mg, 1.18 mmole) and hexylmesylate (1.064 mg, 5.9 mmole) in 15 ml of dry xylene in the course of 15 minutes. The solution was continued to reflux for 30 minutes and then was cooled down to room temperature. Hydrochloric acid (1.2N, 8 ml) was added. The resulting solution was saturated with sodium chloride and extracted with ethyl ether (4×50 ml). The combined ethyl ether extracts were dried (anhydrous MgSO$_4$) and concentrated in vacuo to give an oil. This was chromatographed on a 30 g silica gel (Baker, 60-200 mesh) column, eluting with ethyl acetate-hexane (15:85) to give 360 mg (67.7%) of the title homogeneous (tlc) hexyl ester with consistent $^{13}$C-NMR spectral data.

EXAMPLE 58

[1α,2β(5Z),3β,4α]-7-[3-[(Hexyloxy)methyl]-7-oxabicyclo[2.2.1]hept-2-yl]-3,3-dimethyl-5-heptenoic acid Example 57 ester (360 mg, 1.8 mmole) was heated to reflux with 550 mg of powdered KOH in a mixture of xylene (7 ml) and water (1 ml) under nitrogen for 4 hours. The resulting solution was cooled to room temperature, acidified with 1.2N hydrochloric acid, saturated with sodium chloride, and extracted with ethyl ether (3×50 ml). The combined ethyl ether extracts were dried over anhydrous MgSO$_4$ and evaporated in vacuo to give an oil. This was chromatographed on a 40 g silica gel (Baker, 60-200 mesh) column, eluting successively with ethyl acetate-hexane (1:3) and ethyl acetate to give 250 mg (85.4%) of a homogeneous (tlc) analytical specimen of the title compound with consistent $^1$H-NMR, $^{13}$C-NMR, IR and MS data.

Anal Calcd for $C_{22}H_{38}O_4$: C, 72.09, H, 10.45; Found: C, 72.07; H, 10.37.

H$^1$-NMR Spectrum (CDCl$_3$, FX270): δ 0.90 (t, 3H, J=~8.0, H$_{21}$); 1.05 (s, 6H, H$_{22}$+H$_{23}$); 2.23 (s, 2H, H$_2$); 3.35 (m, 4H, H$_{14}$+H$_{16}$); 4.22 (d, 1H, J=~4.0, Hg); 4.42 (d, 1H, J=~4.0, H$_{12}$); 5.48 (narrow M, 2H, H$_5$+H$_6$)

EXAMPLE 59

[1α,2β(3±,5Z),3β,4α]-7-[3-[(Hexyloxy)methyl]-7-oxabicyclo[2.2.1]hept-2-yl]-3-methyl-5-heptenoic acid

A. 4-Carboxy-3-methylbutyltriphenylphosphonium bromide

A suspension of 5.8 g (0.15 mole) of sodium borohydride in 30 ml of dry tetrahydrofuran was stirred and cooled in an ice bath under nitrogen while 19.21 g (0.15 mole) of 3-methylglutaric anhydride in 120 ml of dry tetrahydrofuran was added in 5 minutes. The ice bath was then removed and stirring was continued for 2 hours. Hydrochloric acid (6N, 60 ml) was added cautiously and the mixture was then concentrated in vacuo. Water (300 ml) was added and the mixture was extracted with ethyl ether. The ethyl ether extract was dried over anhydrous Na$_2$SO$_4$, concentrated in vacuo and distilled (66°, 1 mm Hg) giving 7.7 g (45%) of 3-methylvalerolactone with consistent $^1$H-NMR and $^{13}$C-NMR spectral data. This lactone (4 g, 35.04 mmole) and triphenyl phosphine hydrobromide (12 g, 35.04 mmole) were heated neat under nitrogen at 175° (oil bath temperature) for 3.5 hours. The reaction mixture was cooled to room temperature, diluted with 100 ml of water-ethyl acetate (1:1) and the phases were separated. The aqueous phase was once washed with ethyl acetate, treated with charcoal, filtered and lyophilized to yield 13 g (81.1%) of 4-carboxyl-3-methyl-butyltriphenylphosphonium bromide with consistent $^1$H-NMR spectral data. This was dried (70°, 0.3 mm, 18 hr) prior to use.

B. [1α,2β(5Z),3β,4α]-7-[3-(Hydroxymethyl)-7-oxabicyclo[2.2.1]hept-2-yl]-3-methyl-5-heptenoic acid A slurry of 4-carboxy-3-methylbutyltriphenylphosphonium bromide (1.414 g, 3.0 mmole) and (exo)octahydro-5,8-epoxy-1H-benzopyran-3-ol (340.4 mg, 2 mmole) in 10 ml of dry toluene was chilled to 0° and treated dropwise with a solution of 1.27M potassium t-amylate in toluene (4.7 ml, 5.97 mmole) over 30 minutes. The mixture was then stirred at room temperature overnight. It was then chilled in an ice bath and was treated slowly with glacial acid (0.3 ml) in 2 ml of toluene, diluted with water (5 ml) and acidified with concentrated hydrochloric acid to pH=2.5. The mixture was then diluted with ethyl acetate (20 ml), saturated with sodium chloride and filtered through a bed of HYFLO. The solids were washed with ethyl acetate (2×25 ml). The toluene-ethyl acetate layer was separated and the aqueous layer was extracted with ethyl acetate (3×25 ml). The combined extracts were dried (anhydrous MgSO$_4$) and evaporated in vacuo to give an oil. This was dissolved in 120 ml of dichloromethane-ethyl ether (1:1) and esterified with an etheral solution of diazomethane. The excess diazomethane was destroyed with acetic acid and the solvent was evaporated in vacuo to give the impure title alcohol ester. This was flash-chromatographed on a 200 g silica gel (LPS-1) column, eluting with ethyl acetate-hexane (1:1) to give 450 mg (79.7%) of the title homogeneous (tlc) alcohol ester with consistent $^1$H-NMR spectral data.

C. [1α,2β(3(R,S),5Z),3β,4α]-7-[3-(Hexyloxy)methyl]-7-oxabicyclo[2.2.1]hept-2-yl]-3-methyl-5-heptenoic acid A stirred mixture of powdered KOH (50 mg, 8.9 mmole) in 40 ml of dry xylene was heated to reflux under nitrogen and 20 ml of xylene was removed by distillation. To this was added dropwise a solution of Part B alcohol methyl ester (450 mg, 1.59 mmole) and hexylmesylate (1.44 g, 7.97 mmole) in 15 ml of dry xylene in the course of 15 minutes. The solution was continued to reflux for 30 minutes and then was cooled down to 65°-70°. Hydrochloric acid (1.2N, 8 ml) was then added dropwise. The resulting solution was saturated with sodium chloride and extracted with ethyl ether (4×50 ml). The combined ethyl extracts were dried (anhydrous MgSO$_4$) and concentrated in vacuo to give an oil. This was chromatographed on a 60 g silica gel (Baker, 60-200 mesh) column, eluting successively with ethyl acetate-hexane mixtures (1:4 and 4:6) to give 350 mg (62.4%) of a homogeneous (tlc) analytical specimen of the title compound with consistent $^1$H-NMR, $^{13}$C-NMR, IR and MS data.

Anal Calcd for $C_{21}H_{36}O_4$: C, 71.55; H, 10.30; Found: C, 71.72; H, 10.07.

EXAMPLE 60

[1R-[1α,2β(Z),3β,4α]]-7-[3-[(Hexyloxy)methyl]-7-oxabicyclo[2.2.1]hept-2-yl]-5-heptenoic acid, methyl ester

[1R-[1α,2β(Z),3β,4α]]-7-[3-[(Hexyloxy)methyl]-7-oxabicyclo[2.2.1]hept-2-yl]-5-heptenoic acid (1.35 g, 4 mmole, prepared as described in Examples 41 and 42) was dissolved in Et$_2$O (~30 ml) and a moderate excess of a solution of diazomethane in Et$_2$O was added. After 5 minutes, the excess diazomethane was destroyed by the addition of 2-3 drops of glacial acetic acid. After evaporation of the solvent the residue was flash-chromatographed on a column of silica gel (LP-1, 40 g) eluting the column with ether-hexane (15:85), with tlc monitoring of the fractions, to isolate slightly impure title ester (430 mg, 31%) and pure title ester (958 mg, 68%)[1] as oils with consistent IR, H$^1$-NMR and C$^{13}$-

NMR and $[\alpha]_D^{25}+5.47°$ (C, 2.01; CHCl$_3$). The total yield was 99%.

Anal Calcd for C$_{21}$H$_{36}$O$_4$: C, 71.55; H, 10.29; Found: C, 71.29; H, 10.37.

270 MHz H$^1$-NMR spectrum (CDCl$_3$): δ 0.9 (t, 3H, J=8.5, CH$_3$); 1.3 (s, 8 to 9H, CH$_2$); 2.03 (m, 5H, J=~9.0, CH$_2$CH=); 2.31 (t, 2H, J=8.5, CH$_2$ COO); 3.33 (m, 4H, J=9.0, CH$_2$O); 4.66 (s, 3H, COOCH$_3$); 4.3 (dd, 2H, J=~5.0 (Δ=59), H$_9$ and H$_{12}$); 5.4 (m, 2H, J=~5.0, 14, H$_5$ and H$_6$)

1. The H$^1$-NMR spectrum showed the presence of 3.5 to 4% of the trans-double bond isomer.

EXAMPLE 61

[1R-[1α,2β(2(R,S),5Z),3β,4α]]-7-[3-[(Hexyloxy)methyl]-7-oxabicyclo[2.2.1]hept-2-yl]-2-methyl-5-heptenoic acid, methyl ester A solution of diisopropylamine (4.0 mmole, 404 mg) in dry THF (75 ml) was cooled and stirred in a bath at −78° (dry ice-acetone) under nitrogen and 1.7M butyl-lithium in hexane (3.0 mmole, 1.8 ml) was added. After 5 minutes, a solution of the Example 60 ester (3.0 mmole, 1.05 g) in dry THF (12 ml) was added dropwise in the course of 5 minutes. After another 15 minutes, methyl iodide (neat, 12 mmole, 1.8 g) was added. After 1.5 hours, the solution was allowed to warm to room temperature in the course of about 30 minutes. The mixture was then poured into saturated brine (150 ml) and was extracted with ether (3×80 ml). The extracts were combined, washed with water, dried (MgSO$_4$ anhydrous) and evaporated to afford the crude product as an oil (1.0 g). On the basis of tlc, this was a mixture of essentially two compounds: title ester (major), and Example 60 ester (minor). In addition, minor, more polar impurities were present. This was subjected to a flash chromatography on a silica gel (LPS-1) column to isolate respectively, title ester (650 mg, 59.5%), and Example 60 ester (100 mg, 9.5%).

EXAMPLE 62

[1R-[1α,2β(2(R,S),5Z),3β,4α]]-7-[3-[(Hexyloxy)methyl]-7-oxabicyclo[2.2.1]hept-2-yl]-2-methyl-5-heptenoic acid A solution of the Example 61 ester (0.87 mmole, 320 mg) in methanol (10 ml) was stirred with 3M NaOH (2.0 ml) for 24 hours under an atmosphere of nitrogen. The solution was then acidified with concentrated hydrochloric acid, concentrated in vacuo, diluted with saturated brine and was extracted with ether (3×30 ml). The extracts were combined, washed with water (2×5 ml), dried (MgSO$_4$ anhydrous) and evaporated to afford the title compound as an oil. This was subjected to a column chromatography on silica gel (Baker 60-200 mesh, 15.0 g) eluting the column with Et$_2$O:hexane mixtures (1:1, 1:4 and 3:7) to isolate title acid as a colorless oil (270 mg, 88%), $[\alpha]_D^{25}+3.48°$ (c, 2.3; CHCl$_3$) with consistent elemental analysis, MS, H$^1$- and C$^{13}$-NMR spectral data.

Anal Calcd for C$_{21}$H$_{36}$O$_4$: C, 71.55; H, 71.47; Found: C, 71.47; H, 10.16.

H$^1$-NMR Spectrum (FX-270, CDCl$_3$); 0.83 (t, 3H, J=~8.0, H$_{21}$); 1.13 (d, 3H, J=~8.0, H$_{22}$); 2.42 (q, 1H, J=~8.0, H$_2$); 3.33 (m, 4H, J=~8.0, H$_{14}$+H$_{16}$); 4.14 (d, 1H, J=4.0, H$_{12}$); 4.37 (d, 1H, J=4.0, H$_9$); 5.32 (m, 2H, H$_5$+H$_6$)

EXAMPLE 63

[1R-[1α,2β,3β,4α]]-7-[3-[(Hexyloxy)methyl]-7-oxabicyclo[2.2.1]hept-2-yl]heptanoic acid, methyl ester A solution of the Example 60 methyl ester (550 mg, 1.56 mmole) in CH$_3$OH (25 ml) containing 10% Pd/C (100 mg) was stirred under an atmosphere of hydrogen for 5 hours. The mixture was then filtered through a bed of Celite and was evaporated to afford the title compound as an oil (550 mg, 99.4%), $[\alpha]_D^{23}(-)$ 3.36° (c, 2.32; CHCl$_3$) which was homogeneous by tlc and showed consistent IR, H$^1$-NMR, C$^{13}$-NMR and MS data.

Anal Calcd for C$_{21}$H$_{38}$O$_4$ (MW 354.53): C, 71.14; H, 10.81; Found: C, 71.26; H, 10.98.

H$^1$-NMR(CDCl$_3$, FX-270): δ 0.91 (t, 3H, J=8.0, 21-CH$_3$); 1.31 (broad s, CH$_2$); 2.29 (t, 2H, J=8.0, CH$_2$COOCH$_3$); 3.31 (m, 4H, CH$_2$OCH$_2$); 3.66 (s, 3H, COOCH$_3$); 4.25 (d, 1H, J=~4.0, —CH—O)(H$_9$); 4.41 (d, 1H, J=~4.0, —CH—O)(H$_{12}$)

EXAMPLE 64

[1α,2β(2R,S),3β,4α]]-7-[3-[3-[(Hexyloxy)methyl]-7-oxabicyclo[2.2.1]hept-2-yl]-2-methylheptanoic acid, methyl ester A solution of dry diisopropyl amine (0.561 ml, 4.0 mmole) in dry THF (15 ml) was cooled and stirred in a bath at −78° (dry ice-acetone) under nitrogen and 1.65M n-BuLi in hexane (1.88 ml, 3.1 mmole) was added dropwise. After 5.0 minutes, a solution of the Example 63 methyl ester (1.06 g, 3.0 mmole) in dry THF (10 ml) was added dropwise in about 5 minutes. After another 15 minutes, a solution of dry hexamethylphosphorous amide (HMPA) (2.0 ml) in dry THF (2.0 ml) was added, followed by CH$_3$I (1.68 ml, 27 mmole). After 3 hours, the mixture was poured into cold 10% hydrochloric acid (100 ml) and was extracted with ether (3×100 ml). The extracts were combined, washed with dilute brine, dried (MgSO$_4$ anhydrous), evaporated and the resulting oil was flash chromatographed on silica gel (200 g, LPS-1), eluting with EtOAc-hexane (5:95) to afford, after drying in vacuo, the title compound (870 mg, 82%) as an oil, $[\alpha]_D^{25}=(-)$ 3.73° (c, 3.3; CHCl$_3$) with consistent IR, MS, H$^1$-NMR and C$^{13}$NMR-spectral data.

Anal Calcd for C$_{22}$H$_{40}$O$_4$ (MW 368.56): C, 71.69; H, 10.94; Found: C, 71.43; H, 10.97.

H$^1$-NMR spectrum (CDCl$_3$; FX-270): δ 0.90 (3H, t, J=~7.0, H$_{21}$); 1.14 (3H, d, J=~7.0, H$_{23}$); 2.03 (1H, q, J=~7.0, H$_{13}$); 2.43 (1H, q, J=~7.0, H$_2$); 3.33 (4H, m, —, H$_{14}$+H$_{16}$); 3.67 (3H, s, —, H$_{22}$); 4.23 (1H, d, J=~4.0, H$_9$); 4.39 (1H, d, J=~4.0, H$_{12}$)

EXAMPLE 65

[1R-(1α,2β, 3β,4α]]-7-[3-[(Hexyloxy)methyl]-7-oxabicyclo[2.2.1]hept-2-yl]-2,2-dimethyl-heptanoic acid, methyl ester A solution of dry diisopropyl amine (0.17 ml, 1.18 mmole) in dry THF (10 ml) was cooled and stirred under an atmosphere of dry nitrogen in a bath at −78° (dry ice-acetone) and 1.65M n-BuLi in hexane (0.66 ml, 1.08 mmole) was added dropwise. After 5 minutes, a solution of Example 64 methyl ester (333 mg, 0.9 mmole) in dry THF (5.0 ml) was added dropwise in the course of 5 minutes. After 20 minutes, a solution of dry HMPA (1.0 ml) in dry THF (1.0 ml) and CH$_3$I (0.17 ml, 2.7 mmole) were added. The mixture was then stirred at −78° for 2 hours and was poured into cold 10% hydrochloric acid (75 ml). The mixture was then extracted with ether (3×50 ml). The extracts were combined, washed with dilute brine, dried (MgSO$_4$ anhydrous) and evaporated to afford the product as an oil. This was mixed with the product (50 mg) from an earlier identical reaction and was flash chromatographed on a column of silica gel (200 g, LPS-1) eluting with EtOAc:hexane (5:95) to yield, after evaporation and drying in vacuo, the title methyl ester as an oil (356 mg, 90.8%), $[\alpha]_D^{25}$ (−)2.94° (c, 3.2; CHCl$_3$) with consistent MS, IR, H$^1$-NMR and C$^{13}$-NMR spectral data.

Anal calcd for C$_{23}$H$_{42}$O$_4$ (MW 382.59): C, 72.20; H, 11.07; Found: C, 71.92; C, 11.03.

H$^1$-NMR Spectrum (CDCl$_3$, FX-270): δ 0.90 (3H, t, J=∼7.0, H$_{21}$); 1.17 (6H, s, −, H$_{23}$+H$_{24}$); 2.03 (1H, q, J=∼7.0, H$_{13}$); 3.30 (4H, m, −, H$_{14}$+H$_{16}$); 3.65 (3H, s, −, H$_{22}$); 4.23 (1H, d, J=∼4.0, H$_9$); 4.40 (1H, d, J=∼4.0, H$_{12}$)

EXAMPLE 66

[1R-(1α,2β,3β,4α)]-7-[3-[(Hexyloxy)methyl]-7-oxabicyclo[2.2.1]hept-2-yl]-2,2-dimethylheptanoic acid A solution of Example 65 methyl ester (300 mg, 0.78 mmole) in dioxane (6.0 ml) containing water (5.0 ml) and LiOH.1H$_2$O (360 mg, 8.57 mmole) was refluxed under an atmosphere of nitrogen for 20 hours whereupon complete hydrolysis was noticed by tlc. The mixture was then poured into 10% hydrochloric acid (40 ml) and was extracted with ether (3×40 ml). The extracts were combined, washed with dilute brine, dried (MgSO$_4$ anhydrous) and evaporated. The residual oil was chromatographed on a column of silica gel (Baker 60–200 mesh, 15 g) eluting the column with hexane and Et$_2$O-hexane (1:9 to 7:3) to isolate, after evaporation and drying in vacuo, the title acid as an oil (270 mg, 94%) $[\alpha]_D^{25}$=(−)3.03° (c, 4.1; CHCl$_3$) wit consistent MS, IR, H$^1$-NMR and C$^{13}$-NMR spectral data.

Anal Calcd for C$_{22}$H$_{40}$O$_4$ (MW 368.56): C, 71.69; H, 10.94; Found: C, 71.39; H, 10.68.

H$^1$-NMR Spectrum (CDCl$_3$, FX-270): δ 0.89 (t, 3H, J=∼7.0, H$_{21}$); 1.2 (s, 6H, −, H$_{22}$+H$_{23}$); 2.03 (q, 1H, J=∼7.0, H$_{13}$); 3.33 (m, 4H, −, H$_{14}$+H$_{16}$); 4.26 (d, 1H, J=18 4.0, H$_9$); 4.40 (d, 1H, J=18 4.0, H$_{12}$); ∼9.0 (broad, 1H, −, H$_1$)

EXAMPLE 67

[1R-[1α,2β(Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (dry ice-acetone) under an atmosphere of nitrogen and 1.7M n-BuLi in hexane (1.8 mmole, 1.06 ml) was added. After 5.0 minutes, a solution of [1R-[1α,2β(2(R,S),5Z),3β,4α]]-7-[3-[(hexyloxy)methyl]-7-oxabicyclo[2.2.1]hept-2-yl]-2-methyl-5-heptenoic acid, methyl ester prepared as described in Example 61 (1.77 mmole, 650 mg) in dry THF (6.0 ml) was added in the course of 5 minutes. After 10 minutes, methyl iodide (6.0 mmole, 850 mg) was added. After 1.5 hours, the solution was wamred to room temperature in the course of about 30 minutes. It was then added into 2% hydrochloric acid (75 ml) and was extracted with ether (3×40 ml). The extracts were combined, washed with water (2×20 ml), dried (MgSO$_4$ anhydrous) and evaporated to afford impure title methyl ester and an oil (640 mg, 95%). This was subjected to a flash chromatography on a silica gel (LPS-1) column to yield: title ester (400 mg, 59.3%), a mixture of Example 61 ester and title ester (∼1:1, 140 mg, 11%) and Example 61 ester (80 mg, 12.8%). The title ester was homogeneous (tlc, Et$_2$O-hexane, 1:1) and its H$^1$ and C$^{13}$-NMR spectra were consistent with the structure.

EXAMPLE 68

[1R-[1α,2β(Z),3β,4α]]-7-[3-[(Hexyloxy)methyl]-7-oxabicyclo[2.2.1]hept-2-yl]-2,2-dimethyl-5-heptenoic acid A solution of Example 67 ester (233 mg, 0.612 mmole) in THF (4.0 ml) was mixed with 1N LiOH (4.0 ml) and was stirred under an atmosphere of nitrogen for 24 hours. No hydrolysis was observed by tlc of an acidified (dil. HCl) aliquot. Therefore, solid LiOH·1H$_2$O (12 mmole, 504 mg) was added and the mixture was stirred under reflux for 48 hours resulting in complete hydrolysis (only partial hydrolysis was noted after 24 hours). The mixture was then acidified with concentrated HCl (to pH 2.5) diluted with brine (20 ml) and was extracted with ether (3×20 ml). The extracts were combined, washed with water (2×100 ml), dried (MgSO$_4$ anhydrous) and evaporated to afford the crude product as an oil (210 mg). This was subjected to a column chromatography on silica gel (Baker, 60–200 mesh, 10 g), eluting the column with hexane and Et$_2$O-hexane mixtures (15:85, 1:3) to isolate homogeneous (tlc) title acid as an oil (200 mg, 89%), $[\alpha]_D^{23}$=(+) 1.16° (c, 2.2; CHCl$_3$), with consistent IR, MS, H$^1$- and C$^{13}$-NMR spectral data.

Anal Calcd for C$_{22}$H$_{38}$O$_4$ (MW 366.54): C, 72.08; H, 10.46; Found: C, 72.16; H, 10.37.

H$^1$-NMR Spectrum (FX-270, CDCl$_3$): δ 0.90 (t, 3H, J=∼8.0, H$_{21}$); 1.23 (s, 6H, −, H$_{22}$+H$_{23}$); 2.03 (m, 4H, J=∼8.0, H$_4$+H$_7$); 3.35 (m, 4H, J=∼8.0, H$_{14}$+H$_{16}$); 4.2 (d, 1H, J=∼4.0, H$_9$); 4.43 (d, 1H, J=∼4.0, H$_{12}$); 5.35 (m, 1H, −, H$_5$+H$_6$)

EXAMPLE 69

[1R-[1α,2β(Z),3β,4α]]-7-[3-[(Hexyloxy)methyl]-7-oxabicyclo[2.2.1]hept-2-yl]-2,2-dimethyl-5-heptenoic acid, methyl ester A solution of dry diisopropylamine (9.0 mmole, 1.26 ml, 911 mg) in dry THF (50 ml) was cooled and stirred in a bath at −78° (dry ice-acetone) and 1.65M n-butyllithium in hexane (7.1 mmole, 4.30 ml) was added. After 10 minutes, a solution of Example 61 methyl ester (2.34 g, 6.38 mmole) in dry THF (10 ml) was added in the course of 5 minutes. After 15 minutes, a solution of dry HMPA (2.0 ml) in dry THF (2.0 ml) and CH$_3$I (18 mmole, 2.56 g) were added. After 2 hours, the mixture was poured into cold 10% hydrochloric acid (100 ml) and most of the THF was removed in vacuo at room temperature. The mixture was then extracted with ether (3×70 ml), the extracts were combined, washed successively with 10% hydrochloric acid, dilute brine and water, dried (MgSO$_4$ anhydrous) and evaporated to afford the crude product as an oil (2.42 g). This was flash chromatographed on a column of silica gel (200 g, LPS-1), eluting the column with Et$_2$O-hexane (1:9) to isolate, after drying in vacuo, the homogeneous (tlc) title compound as an oil (2.30 g, 94.7%), $[\alpha]_D^{25}$(+)1.97° (c, 3.56; CHCl$_3$) with consistent MS, IR, H$^1$-NMR and C$^{13}$-NMR spectral data.

Anal Calcd for $C_{23}H_{40}O_4$ (MW 380.57): C, 72.58; H, 10.59; Found: C, 72.58; H, 10.50.

$H^1$-NMR Spectrum (FX-270, $CDCl_3$): δ 0.90 (t, 3H, J=~7.0, $H_{21}$); 1.21 (s, 6H, —, $H_{22}+H_{23}$); 3.35 (m, 4H, —, $H_{14}+H_{16}$); 3.68 (s, 3H, —, $H_{24}$);

$\begin{cases} 4.18 \text{ (s, 0.86H, J} \approx 4.0, H_9) \\ 4.23 \text{ (d, 0.14H, } H_9 \text{ of 14\% of 5,6-trans-isomer)} \end{cases}$ 4.40 (d, 1H, J=~4.0, $H_{12}$); 5.35 (m, 2H, —, $H_5+H_6$)

The following additional compounds as outlined in the Table set out below were prepared following the procedures described in the specification and working Examples

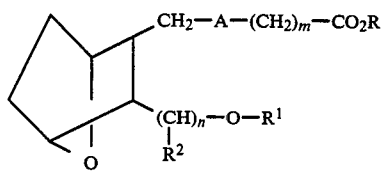

| Ex. No. | $CH_2$—A—$(CH_2)_m$COOR | $(CH)_n$—O—$R^1$ / $R^2$ | Stereochemistry |
|---|---|---|---|
| 70. | 5-heptenoic acid | hexyloxymethyl | 1R—(1α,2β,3β,4α) |
| 71. | heptanoic acid | hexyloxymethyl | 1R—(1α,2β,3β,4α) |
| 72. | heptanoate methyl ester | hexyloxymethyl | 1R—(1α,2β,3β,4α) |
| 73. | 5-heptenoate methyl ester | hexyloxymethyl | 1R—(1α,2β,3β,4α) |
| 74. | 5-heptenoic acid | hexyloxymethyl | (±)-(1α,2β,3β,4α) |
| 75. | 5-heptenoic acid | octyloxymethyl | (±)-(1α,2β,3β,4α) |
| 76. | 2-heptenoic acid | hexyloxymethyl | 1R—(1α,2β,3β,4α) |
| 77. | 5-heptenoic acid | hexyloxymethyl | (±)-(1α,2α,3β,4α) |
| 78. | 5-heptenoic acid | 2-methylhexyloxymethyl | (±)-(1α,2β,3β,4α) |
| 79. | 5-heptenoic acid | hexyloxymethyl | (±)-(1α,2β,3α,4α) |
| 80. | 5-heptenoic acid | phenylpropyloxymethyl | (±)-(1α,2β,3β,4α) |
| 81. | 5-heptenoic acid | hexyloxymethyl | (±)-(1α,2α,3α,4α) |
| 82. | 5-heptenoic acid | hexyloxymethyl | 1S—(1α,2β,3β,4α) |
| 83. | 5-heptenoic acid | pentyloxymethyl | (±)-(1α,2β,3β,4α) |
| 84. | 5-heptenoic acid | cyclohexylmethoxymethyl | (±)-(1α,2β,3β,4α) |
| 85. | 6-heptenoic acid | hexyloxymethyl | (±)-(1α,2β,3β,4α) |
| 86. | 5-heptenoic acid | methoxymethyl | 1R—(1α,2β,3β,4α) |
| 87. | pentanoic acid | hexyloxymethyl | (±)-(1α,2β,3β,4α) |
| 88. | 5-heptenoic acid | 1-(hexyloxy)-ethyl | (±)-(1α,2β,3β,4α) |
| 89. | 5-heptenoic acid | 1-methylhexyloxymethyl | (±)-(1α,2β,3β,4α) |
| 90. | 5-heptenoic acid | pentyloxymethyl | (±)-(1α,2β,3β,4α) |
| 91. | 5-heptenoic acid | heptyloxymethyl | (±)-(1α,2β,3β,4α) |

What is claimed is:

1. A compound having the structural formula

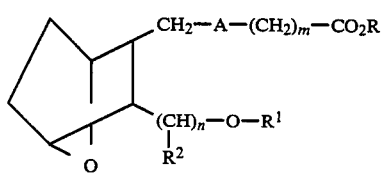

and including all stereoisomers thereof, wherein
A is —CH=CH— or —$(CH_2)_2$—;
m is 1 to 8; n is 1 to 4;
R is hydrogen, lower alkyl, alkali metal or tris(hydroxymethyl)aminomethane; $R^1$ is lower alkyl, aryl, aralkyl, cycloalkyl or cycloalkylalkyl; and $R^2$ is H or unsubstituted lower alkyl, but where $R^2$ is unsubstituted lower alkyl, n is 1, wherein the term lower alkyl or alkyl by itself or as part of another group contains 1 to 12 carbons and is unsubstituted or substituted with halo, trifluoromethyl, alkoxy, alkylthio, haloaryl, alkylamino, cycloalkyl or alkylcycloalkyl;

the term aryl by itself or as part of another group contains 6 to 10 carbons and is unsubstituted or substituted with lower alkyl, halogen or lower alkoxy groups;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups.

2. The compound as defined in claim 1 wherein A is —CH=CH—.

3. The compound as defined in claim 1 wherein R is H.

4. The compound as defined in claim 1 wherein n is 1.

5. The compound as defined in claim 1 wherein n is 2.

6. The compound as defined in claim 1 wherein n is 3 or 4.

7. The compound as defined in claim 1 wherein n is 1 and $R^2$ is methyl.

8. The compound as defined in claim 1 wherein A is —CH=CH—, m is 2 to 4, n is 1 or 2, R is H and $R^1$ is lower alkyl or cycloalkyl and $R^2$ is H or methyl.

9. The compound as defined in claim 1 wherein A is —CH=CH—, m is 3, n is 1, R is H, CH₃ or C₆H₁₃, R¹ is lower alkyl and R² is H or methyl.

10. The compound as defined in claim 1 having the name [1β,2α(5Z),3α,4β]-7-[3-[(hexyloxy)methyl]-7-oxabicyclo[2.2.1]hept-2-yl]-5-heptenoic acid or its hexyl ester, including all stereoisomers thereof.

11. The compound as defined in claim 1 having the name [1β,2α(5Z),3α,4β]-7-[3-[2-(pentyloxy)-ethyl]-7-oxabicyclo[2.2.1]hept-2-yl]-5-heptenoic acid or its pentyl ester, including all stereoisomers thereof.

12. The compound as defined in claim 1 having the name [1β,2α(5Z),3α,4β]-7-[(3-phenylpropoxy)-methyl]-7-oxabicyclo[2.2.1]hept-2-yl]-5-heptenoic acid or its phenylpropyl ester, including all stereoisomers thereof.

13. The compound as defined in claim 1 having the name [1β,2α(5Z),3α,4β]-7-[3-[(octyloxy)methyl]-7-oxabicyclo[2.2.1]hept-2-yl]-5-heptenoic acid or its octyl ester, including all stereoisomers thereof.

14. The compound as defined in claim 1 having the name [1β,2α(5Z),3α,4β]-7-[3-(cyclohexylmethoxy)methyl]-7-oxabicyclo[2.2.1]hept-2-yl]-5-heptenoic acid or its cyclohexylmethyl ester, including all stereoisomers thereof.

15. The compound as defined in claim 1 having the name [1β,2α(Z),3β,4β]-7-[3-[(hexyloxy)methyl]-7-oxabicyclo[2.2.1]hept-2-yl]-5-heptenoic acid or its methyl ester, including all stereoisomers thereof.

16. The compound as defined in claim 1 having the name [1β,2β(Z),3α,4β]-7-[3-[(hexyloxy)methyl]-7-oxabicyclo[2.2.1]hept-2-yl]-5-heptenoic acid or its methyl ester, including all stereoisomers thereof.

17. The compound as defined in claim 1 having the name 1R-[1α,2β(Z),3β,4α]]-7-[3-[(hexyloxy)methyl]-7-oxabicyclo[2.2.1]hept-2-yl]-5-heptenoic acid, its tris(hydroxymethyl)aminomethane salt or its hexyl ester, including all stereoisomers thereof.

18. The compound as defined in claim 1 having the name [1α,2β(Z),3β,4α]-7-[3-[[(2-methylhexyl)oxy]methyl]-7-oxabicyclo[2.2.1]hept-2-yl]-5-heptenoic acid or its methyl ester, including all stereoisomers thereof.

19. The compound as defined in claim 1 having the name [1β,2α(Z),3α,4β]-7-[3-[1-(hexyloxy)ethyl]-7-oxabicyclo[2.2.1]hept-2-yl]-5-heptenoic acid (fast moving isomer) or its hexyl ester, including all stereoisomers thereof.

20. The compound as defined in claim 1 having the name [1α,2α(Z),3α,4α]-7-[3-[(hexyloxy)methyl]-7-oxabicyclo[2.2.1]hept-2-yl]-5-heptenoic acid or its hexyl ester, including all stereoisomers thereof.

21. The compound as defined in claim 1 having the name [1R-[1α,2β,3β,4α]]-7-[3-[(hexyloxy)methyl]-7-oxabicyclo[2.2.1]hept-2-yl]-heptanoic acid including all stereoisomers thereof.

22. The compound as defined in claim 1 having the name [1α,2β(Z),3β,4α]-7-[3-[[(1-methylhexyl)oxy]methyl]-7-oxabicyclo[2.2.1]hept-2-yl]-5-heptenoic acid (fast moving isomer) or its 1-methylhexyl ester, including all stereoisomers thereof.

23. The compound as defined in claim 1 having the name [1R-[1α,2β(Z),3β,4α]-7-[3-(methoxymethyl)-7-oxabicyclo[2.2.1]hept-2-yl]-5-heptenoic acid including all stereoisomers thereof.

24. The compound as defined in claim 1 having the name [1α,2β(5Z),3β,4α]]-7-[3-[(hexyloxy)methyl]-7-oxabicyclo[2.2.1]hept-2-yl]-3,3-dimethyl-5-heptenoic acid or its hexyl ester and including all stereoisomers thereof.

25. The compound as defined in claim 1 having the name [1R-[1α,2β(5Z),3β,4α]]-7-[3-[(hexyloxy)methyl]-7-oxabicyclo[2.2.1]hept-2-yl]-3,3-dimethyl-5-heptenoic acid and including all stereoisomers thereof.

26. The compound as defined in claim 1 having the name [1R-[1α,2β(Z),3β,4α]]-7-[3-[(hexyloxy)methyl]-7-oxabicyclo[2.2.1]hept-2-yl]-5-heptenoic acid or its methyl ester and including all stereoisomers thereof.

27. The compound as defined in claim 1 having the name [1R-[1α,2β(5Z),3β,4α]]-7-[3-[(hexyloxy)methyl]-7-oxabicyclo[2.2.1]hept-2-yl]-2,2-dimethyl-5-heptenoic acid or its methyl ester and including all stereoisomers thereof.

28. The compound as defined in claim 1 having the name [1R-[1α,2β,3β,4α]]-7-[3-[(hexyloxy)methyl]-7-oxabicyclo[2.2.1]hept-2-yl]heptanoic acid and or its methyl ester and including all stereoisomers thereof.

29. The compound as defined in claim 1 having the name [1R-[1α,2β(±),3β,4α]]-7-[3-[(hexyloxy)methyl]-7-oxabicyclo[2.2.1]hept-2-yl]-2-methyl heptanoic acid or its methyl ester and including all stereoisomers thereof.

30. The compound as defined in claim 1 having the name [1R-[1α,2β,3β,4α]]-7-[3-[(hexyloxy)methyl]-7-oxabicyclo[2.2.1]hept-2-yl]-2,2-dimethyl heptanoic acid or its methyl ester and including all stereoisomers thereof.

31. The compound as defined in claim 1 having the name [1R-[1α,2β(Z),3β,4α]]-7-[3-[(hexyloxy)methyl]-7-oxabicyclo[2.2.1]hept-2-yl]-2,2-dimethyl-5-heptenoic acid or its methyl ester and including all stereoisomers thereof.

32. A method of inhibiting platelet aggregation and bronchoconstriction, which comprises administering to the circulatory system of a mammalian host an effective amount of a compound as defined in claim 1 or a pharmaceutically acceptable salt thereof.

33. The method as defined in claim 32 wherein said compound is administered in an amount within the range of from about 1 to about 100 mg/kg.

34. A composition for inhibiting platelet aggregation and bronchoconstriction comprising an effective amount of a compound as defined in claim 1 or a pharmaceutically acceptable salt thereof, and a pharmaceutically acceptable carrier thereof.

35. A method of inhibiting platelet aggregation, inhibiting bronchoconstriction, treating inflammation or relieving pain, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,582,854      Page 1 of 2
DATED      : April 15, 1986
INVENTOR(S): Steven E. Hall et al.

It is certified that error appears in the above-identified patent and that said Letters Patent is hereby corrected as shown below:

Column 3, in reaction sequence "c", structure V or V' should read

--
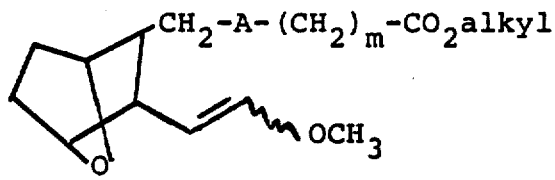

V or V'                    --.

Column 9, line 57, structure Ih should read

--
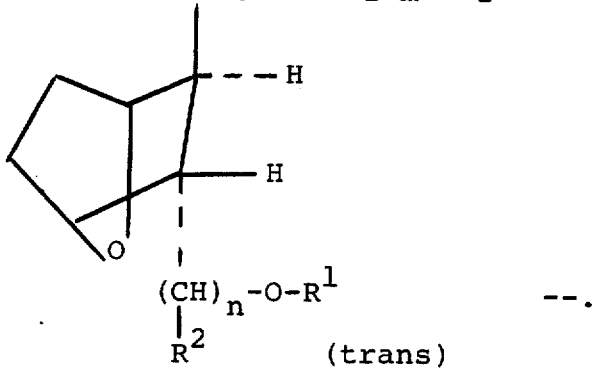

(trans)                    --.

UNITED STATES PATENT AND TRADEMARK OFFICE
CERTIFICATE OF CORRECTION

PATENT NO. :  4,582,854                    Page 2 of 2

DATED      :  April 15, 1986

INVENTOR(S):  Steven E. Hall et al.

It is certified that error appears in the above-identified patent and that said Letters Patent is hereby corrected as shown below:

```
Column 19, line 14, before "1β" insert --[--.
Column 24, line 38, "octanhydro" should read --octahydro--.
Column 38, line 24, "[3-[3-" should read --[3- --.
```

Signed and Sealed this

Thirteenth Day of January, 1987

*Attest:*

DONALD J. QUIGG

*Attesting Officer*     *Commissioner of Patents and Trademarks*